(12) United States Patent
Rozen et al.

(10) Patent No.: US 7,919,526 B2
(45) Date of Patent: Apr. 5, 2011

(54) STRUCTURED TRIGLYCERIDES AND EMULSIONS COMPRISING SAME

(75) Inventors: Geila Rozen, Haifa (IL); Irit Shochat, Timrat (IL)

(73) Assignee: HTL High-Tech Lipids Ltd., D.N. Misgav (IL)

( * ) Notice: Subject to any disclaimer, the term of this patent is extended or adjusted under 35 U.S.C. 154(b) by 965 days.

(21) Appl. No.: 10/591,734

(22) PCT Filed: Mar. 3, 2005

(86) PCT No.: PCT/IL2005/000257
§ 371 (c)(1),
(2), (4) Date: May 1, 2007

(87) PCT Pub. No.: WO2005/084129
PCT Pub. Date: Sep. 15, 2005

(65) Prior Publication Data
US 2007/0281993 A1  Dec. 6, 2007

(51) Int. Cl.
*A61K 31/355* (2006.01)
(52) U.S. Cl. .................. 514/458; 514/560; 554/227
(58) Field of Classification Search .................. 514/458, 514/560; 554/227
See application file for complete search history.

(56) References Cited

U.S. PATENT DOCUMENTS

| | | | |
|---|---|---|---|
| 4,567,045 A | 1/1986 | Lyons | 424/195.1 |
| 4,607,052 A | 8/1986 | Mendy et al. | |
| 4,645,741 A | 2/1987 | Inada | 435/134 |
| 4,871,768 A | 10/1989 | Bistrian et al. | 514/547 |
| 4,906,664 A | 3/1990 | Bistrain | 514/552 |
| 5,081,105 A | 1/1992 | Bristrain | 514/2 |
| 5,232,843 A | 8/1993 | Bosley et al. | 435/135 |
| 5,661,180 A | 8/1997 | DeMichele et al. | 514/547 |
| 5,773,266 A | 6/1998 | Bosley et al. | 435/134 |
| 5,962,712 A | 10/1999 | DeMichele et al. | 554/224 |
| 6,369,252 B1 | 4/2002 | Akoh | 554/227 |
| 6,518,049 B1 | 2/2003 | Haraldsson et al. | 435/134 |
| 6,537,787 B1 | 3/2003 | Breton | 435/134 |
| 6,596,520 B1 | 7/2003 | Friedrich et al. | 435/135 |
| 6,605,452 B1 | 8/2003 | Basheer | 435/134 |

FOREIGN PATENT DOCUMENTS

| | | | |
|---|---|---|---|
| EP | 271909 | * | 6/1988 |
| EP | 0271909 | | 6/1988 |
| EP | 265699 | * | 9/1993 |

(Continued)

OTHER PUBLICATIONS

Klang et al.,"Design and evaluation of submicron emulsions as colloidal drug carriers for intravenous administration", Drug Targeting and Delivery (1998), 9(Submicron Emulsions in Drug Targeting and Delivery), 119-152.*

(Continued)

*Primary Examiner* — Deborah D Carr
(74) *Attorney, Agent, or Firm* — Winston & Strawn LLP

(57) ABSTRACT

The present invention relates to structured triglyceride, to parental nutrition emulsions comprising same, and use thereof. In particular, the invention relates to structured triglycerides comprising at least one medium chain $C_6$-$C_{12}$ fatty acid and at least one fatty acid selected from the group consisting of long chain $C_{14}$-$C_{18}$ or very long chain $C_{20}$-$C_{22}$ fatty acids, preferably each fatty acid is present in a predetermined position of the glycerol backbone. The parenteral nutrition emulsions are particularly useful for nourishing preterm- and term-infants, children, critically ill patients, and cancer patients.

41 Claims, 3 Drawing Sheets

FOREIGN PATENT DOCUMENTS

| EP | 0265699 B1 | | 9/1993 |
|---|---|---|---|
| EP | 0965578 | | 12/1999 |
| EP | 965578 | * | 4/2003 |
| WO | WO03/033632 A1 | | 4/2003 |

OTHER PUBLICATIONS

Rubin et al., "Structured triacylglycerol emulsion, containing both medium- and long-chain fatty acids, in long-term home parenteral nutrition: a double-blind randomized cross-over study", Nutrition, vol. 16, Issue 2, pp. 95-100 (2000).

Sandstrom et al., "Structured triglycerides were well tolerated and induced increased whole body fat oxidation compared with long-chain triglycerides in postoperative patients", Journal of Parenteral and Enteral Nutrition, vol. 19, Issue 5, pp. 381-386 (1995).

Krumiel et al., "Parenteral structured triglyceride emulsion improves nitrogen balance and is cleared faster from the blood in moderately catabolic patients", Journal of Parenteral and Enteral Nutrition, vol. 25, Issue 5, pp. 237-244 (2001).

Chambrier et al., "Medium- and long-chain triacylglycerols in postoperative patients: structured lipids versus a physical mixture". Nutrition, vol. 15, Issue 4, pp. 274-277 (1999).

Sugihara et al., "Characterization of Geotrichum candidum lipase III with some preference for the inside ester bond of triglyceride", Applied Microbiology and Biotechnology, vol. 40, Nos. 2-3, pp. 279-283 (1993).

Ota et al., "Tributyrin specifically induces a lipase with a preference for the sn-2 position of triglyceride in Geotrichum sp. FO401B", Biosci Biotechnol Biochem, vol. 64(11): pp. 2497-2499 (2000).

J. Nagata, et al., "Effects of Highly Purified Structured Lipids Containing Medium-Chain Fatty Acids And Linoleic Acid On Lipid Profiles In Rats", Biosci Biotechnol Biochem, vol. 67(9) pp. 1937-1943 (2003).

J. Stein, "Chemically Defined Structured Lipids: Current Status And Future Directions In Gastrointestinal Diseases", Int. J. Colorectal Dis., vol. (14): pp. 79-85 (1999).

* cited by examiner

STRUCTURED TRIGLYCERIDES AND EMULSIONS COMPRISING SAME

FIELD OF INVENTION

The present invention relates to structured triglycerides, to emulsions comprising same suitable for parenteral nutrition, and use thereof. In particular, the invention relates to structured triglycerides comprising at least one medium chain $C_6$-$C_{12}$ fatty acid and at least one fatty acid selected from long chain $C_{14}$-$C_{18}$ and very long chain $C_{20}$-$C_{22}$ fatty acids, preferably each fatty acid being in a predetermined position of the glycerol backbone. The parenteral nutrition emulsions are particularly useful for nourishing preterm and term infants, children, critically ill patients, and cancer patients.

BACKGROUND OF THE INVENTION

Lipids have been used as an integral component of parenteral nutrition over the last four decades. Lipids provide essential fatty acids for cellular structures, specifically cell membranes, and for precursors of prostaglandins, leukotrienes, thromboxanes and other eicosanoids. They constitute a source of energy, take part in various biosynthetic pathways, and are carriers of fat-soluble vitamins. As such, lipids play an important role in metabolic and immune processes, in the development and function of the central nervous system and the retina.

Fatty acids (FA) differ from one another by the number of carbon atoms, their saturation or degree of non-saturation, the positions of unsaturated bonds, and whether these bonds are cis or trans. All of these variables are relevant to the nutritional value or benefit derived from triglycerides containing these acids. In addition, the enzymatic cleavage of the triglycerides is affected by the type and position of the fatty acids on the glycerol backbone.

Fatty acids in general are divided into four groups: short chain FA, medium chain FA (MCFA), long chain FA (LCFA), and very long chain FA (VLCFA). Fatty acids are also classified by the presence, number, and location of double bonds. This classification divides FA into three groups: saturated FA (no double bonds), monounsaturated FA (one double bond) and polyunsaturated FA (2 double bonds and more). Further classification of the polyunsaturated FA is characterized by the placement of the carbon preceding the first double bond from the terminal methyl carbon: n-3 or ω-3 FA, n-6 or ω-6 FA and n-9 or ω-9 FA. These differences determine the various characteristics of FA and therefore their specific functions.

Lipid Emulsions

The need for lipids as essential and integral component of parenteral nutrition (PN) emerged from the observations of the clinical symptoms following use of fat free PN. These clinical symptoms included hemorrhagic dermatitis, skin atrophy, hyperglycemia, weight loss, decrease of immune function, increase of catabolism, etc.

The first generation of lipid emulsions was based on pure long chain triglycerides (LCT) derived from soybean oil and safflower oil. Their administration prevented some of the symptoms of fatty acid deficiency. Nevertheless, patients that received these lipid emulsions showed impaired function of lymphocytes and of the reticuloendothelial system, depressed T-cell counts, increased oxygen free radical production, elevation of liver enzymes, hypertriglyceridemia, and suffered from infections.

The next generation of lipid emulsions contained 50% medium chain triglycerides (MCT) and 50% LCT. These emulsions have many advantages compared to pure LCT emulsions, for example, they are an efficient energy source, they are more soluble, rapidly hydrolyzed by lipases, quickly eliminated from blood, rapidly oxidized, and have smaller particle size. As the MCFA are all saturated, they are not subjected to peroxide formation and therefore they do not impair the immune and reticuloendothelial systems. Patients receiving MCT/LCT emulsions demonstrate a better nitrogen balance and a better protein sparing effect.

Another attempt to overcome the disadvantages of pure LCT emulsions was to use olive oil, rich in monounsaturated oleic acid (18:1 ω-9). Olive oil based emulsions were shown to be well-tolerated, more suitable for preventing lipid peroxidation, and maintained a normal essential FA status. It was also demonstrated that olive oil emulsions contain primarily alpha tocopherol, the more biologically active tocopherol, while soybean oil emulsions contain predominantly gamma tocopherol, which has little protection against lipid peroxidation. When the composition and peroxidation of lipoproteins were compared in children receiving olive oil or soybean oil emulsions, it was found that administration of olive oil emulsions resulted in a decreased oxidative stress. Gobel et al., and Goulet et al., showed the advantages of olive oil emulsions compared to other LCT emulsions in preterm infants and in children (Gobel Y., et al., J. Pediatr. Gastroenterol. Nutr. 37(2): 161-167, 2003; Goulet, O., et al., Am. J. Clin. Nutr. 70(3): 338-345, 1999). Oleic acid, and in general the ω-9 fatty acids, have been shown to contribute to brain development and function as they are a major component of the white matter and myelin.

The beneficial effects of ω-3 fatty acids derived from fish oil in enteral feeding prompted their inclusion in parenteral nutrition. The most successful regimen was achieved by the combination of 50% MCT, 40% soybean oil and 10% fish oil. This regimen demonstrated an improvement in the immune system function of surgical and critically ill patients, an improvement of FA profile in cell membranes, anti-inflammatory and anti-coagulation effects, a normalization of plasma triglycerides (TG) and cholesterol, and a reduction in blood pressure.

Structured Triglycerides

Lipid emulsions containing randomized structured triglycerides (STG) have been obtained by mixing MCT and LCT oils and heating the mixture in the presence of a catalyst. During this process, MCFA and LCFA can be exchanged randomly on the glycerol backbone of both oils. The new TG thus formed contains both long and medium chain FA on the same glycerol, randomly distributed. This kind of triglycerides are rapidly hydrolyzed by lipases, and hence are better cleared from the blood stream.

Many clinical studies have demonstrated the safety and the advantages of STG emulsions. Sandstrom et al., demonstrated that STG emulsions administered to postoperative patients were rapidly cleared from the plasma, rapidly oxidized, and were not associated with any side effects (Sandstrom, R., et al., JPEN 19 (5): 381-386, 1995). Provision of STG caused a significantly higher whole body fat oxidation compared to LCT. Rubin et al, demonstrated that STG appear to be safe and well tolerated on a long term basis in patients on home parenteral nutrition and suggested that STG emulsions may be associated with possible reduction in liver dysfunction (Rubin, M., et al., Nutrition, 16: 95-100, 2000).

Kruimel et al., compared the effect of STG versus physical mixture of MCT and LCT on the nitrogen balance of moderately catabolic postoperative patients. Over a period of 5 days the cumulative nitrogen balance was less negative in the STG group (Krumiel, J. W., et al., JPEN 25(5): 237-244, 2001).

This difference can be explained by better utilization of the STG fatty acids for energy and better clearance from the blood (ibid.). Chambrier et al., compared the effect of STG vs. a physical mixture of MCT-LCT on liver function in postoperative patients. A significant increase in liver enzymes and in plasma TG was found to occur in patients administered with the physical mixture of MCT-LCT, while no changes in liver function nor in plasma TG level were found to occur in patients administered with STG (Chambrier, C., et al., Nutrition, 15: 274-277, 1999).

U.S. Pat. No. 4,871,768 discloses a synthetic triglyceride comprising a glycerol backbone having three fatty acids attached thereto, wherein at least one fatty acid is selected from ω3 fatty acids and at least one fatty acid is selected from $C_8$-$C_{10}$ fatty acids. The ω3 fatty acids are derived from plant oils, marine plankton oils, fungal oils, or fish oils. U.S. Pat. No. 4,871,768 also discloses a dietary supplement comprising 10 to 40% by weight of an oily fraction, the oily fraction comprises 10 to 90% by weight of the synthetic triglyceride. The synthetic triglyceride in the dietary supplement according to U.S. Pat. No. 4,871,768 further comprises ω9 fatty acids. Yet, the necessity of docosahexaenoic acid (DHA) and arachidonic acid in the synthetic triglyceride, and the necessity of vitamin E in the dietary supplement have not been indicated nor the optimal ratio of ω6 to ω3.

U.S. Pat. No. 4,906,664 discloses a method for providing nutritional support to patients suffering from cancer cachexia. The method comprises the step of parenteral administration of a diet containing a structured lipid. The structured lipid according to U.S. Pat. No. 4,906,664 is a triglyceride wherein at least one of the chains is a medium chain fatty acid, at least one of the chains is an ω3 long chain fatty acid, and the other chain is selected from the group consisting of medium chain fatty acids and long chain fatty acids. The ratio of long chain fatty acids to medium chain fatty acids is about 1:1. The long chain fatty acids should be primarily ω3 and ω6 fatty acids, with sufficient ω6, preferably in the form of linoleic acid.

U.S. Pat. No. 5,081,105 discloses a method of treating sarcomas in a patient through the use of nutritional support therapy comprising the step of parenterally administering a diet including a structured lipid. The structured lipid according to U.S. Pat. No. 5,081,105 is a triglyceride where one of the chains is a medium chain fatty acid, a second chain is a ω3 fatty acid, and the third chain is selected from H, OH, short, medium, and long fatty acids.

U.S. Pat. No. 5,962,712 discloses a family of structured lipids, one of the fatty acid residues is selected from the group consisting of gamma linolenic acid (GLA) and dihomogamma linolenic acid (DHGLA). A second fatty acid residue is selected from $C_{18}$-$C_{22}$ n-3 fatty acids, and the third fatty acid residue is selected from $C_6$-$C_{12}$ fatty acids. The simultaneous presence of $C_{18}$-$C_{22}$ n-3 fatty acid residues and GLA or DHGLA may serve to minimize the elongation of GLA and DHGLA to arachidonic acid. The long chain polyunsaturated n-3 fatty acids will purportedly shift the prostaglandin metabolism away from pro-inflammatory prostanoids to non-inflammatory prostanoids, having beneficial effects in treating inflammation and infection. U.S. Pat. No. 5,661,180 discloses a method of modulating metabolic response to trauma and disease states in a patient comprising the step of administering a dietary structured lipid as disclosed in U.S. Pat. No. 5,962,712.

There is an unmet need for structured triglycerides designed to provide improved enteral or parenteral nutrition, which is easily assimilated by infants, children, and patients suffering severe stress or chronic illness and which is optimized to address developmental and immunological needs.

SUMMARY OF THE INVENTION

It is now disclosed that parenteral nutrition emulsions comprising structured triglycerides comprising medium chain (MCFA), long chain (LCFA), and very long chain fatty acid residues (VLCFA), are highly advantageous for parenteral nutrition, particularly for preterm- and term-infants, children, critically ill patients, and cancer patients. The present invention provides parenteral nutrition emulsions comprising structured triglycerides having specific beneficial ratios of MCFA, LCFA and VLCFA.

The present invention further provides parenteral nutrition emulsions comprising structured triglycerides wherein the position of the fatty acid residues on the glycerol backbone is predetermined.

The present invention discloses for the first time parenteral nutrition emulsions comprising structured triglycerides comprising at least one MCFA, and at least one LCFA or VLCFA, the LCFA or VLCFA is esterified primarily at the external position of the glycerol backbone. According to some embodiments, the VLCFA are selected from arachidonic acid (AA; 20:4 ω-6), eicosapentaenoic acid (EPA; 20:5 ω-3), docosahexaenoic acid (DHA; 22:6 ω-3), or any combination thereof. The parenteral nutrition emulsions provide high nutritional advantage, improve the immune system function, and have beneficial effects on the structure and function of cell membranes, on the development and function of the brain, CNS and retina, on the regulation of blood pressure, and on coagulation processes. The parenteral nutrition emulsions of the invention are, therefore, particularly beneficial for preterm- and term-infants, children, cancer patients, and critically ill patients.

As the structured triglycerides of the present invention comprise at least one MCFA and at least one LCFA or VLCFA on the same glycerol backbone, the physical characteristics of these structured triglyceride emulsions are improved compared to those of pure LCT or mixed LCT/MCT emulsions. Thus, the structured triglyceride emulsions of the invention achieve lower particle size than mixed LCT/MCT emulsions and consequently they can be filtered through a filter of a pore size of 0.22 μm. The structured triglyceride emulsions of the invention are also more soluble and more stable than mixed LCT/MCT emulsions. Additionally, as the LCFA and the VLCFA are located preferably at the external position of the glycerol backbone, the clearance of these fatty acids from the blood is faster than if they were positioned on the internal position, and therefore these structured triglycerides enable maintenance of a regulated blood triglyceride level.

It is also disclosed that a low ratio of ω-6 to ω-3 fatty acids, particularly an ω6/ω-3 ratio lower than 2:1 in the parenteral nutrition emulsions comprising the structured triglycerides provides beneficial effects on brain development in preterm- and term-infants, and in children. The low ω-6/ω3 ratio provides beneficial effects on the immune system and on the heart function and these effects are particularly essential in critically ill patients and in cancer patients. A decrease of the ω-6 fatty acid intake and an increase of the ω-3 fatty acid intake with no supplementation of sufficient amounts of AA and DHA may impair various biological processes such as blood coagulation cascades and regulation of blood pressure. It may also impair the chemical and physical characters of cell membranes, and the development and function of the brain, CNS, and retina. Therefore, the presence of AA and DHA in the structured triglycerides of the invention is of high importance both for infants, children, and adult patients.

It is further disclosed that inclusion of monounsaturated oleic acid (18:1 ω-9) in the structured triglycerides provides superior properties compared to polyunsaturated fatty acids, as the former is required for the structure and function of the brain. In addition, oleic acid is less susceptible to peroxide formation compared to polyunsaturated fatty acids, and therefore inclusion of this fatty acid provides less exposure to peroxidation damages.

It is also disclosed that addition of vitamin E, particularly alpha tocopherol, to the parenteral nutrition emulsions provides protection of the subject nourished with said parenteral nutrition emulsions against peroxide formation, and therefore protects the subject from peroxidation damages.

According to one aspect, the present invention provides a structured triglyceride comprising a glycerol backbone having three fatty acid residues esterified thereto, wherein at least one fatty acid residue is selected from the group consisting of $C_6$-$C_{12}$ fatty acids and active derivatives thereof, and at least one fatty acid residue is selected from the group consisting of $C_{14}$-$C_{18}$ fatty acids, $C_{20}$-$C_{22}$ fatty acids, and active derivatives thereof, with the proviso that a $C_{18}$-$C_{22}$ ω3 fatty acid residue is not present on the same glycerol backbone together with gamma linolenic acid or dihomogamma linolenic acid.

According to another aspect, the present invention provides a structured triglyceride comprising a glycerol backbone having three fatty acid residues esterified thereto, wherein at least one fatty acid residue is selected from the group consisting of $C_6$-$C_{12}$ fatty acids and active derivatives thereof in the internal position of the glycerol backbone, and at least one fatty acid residue is selected from the group consisting of $C_{14}$-$C_{18}$ fatty acids, $C_{20}$-$C_{22}$ fatty acids, and active derivatives thereof in an external position of the glycerol backbone.

According to some embodiments, the $C_{14}$-$C_{18}$ fatty acids are selected from the group consisting of saturated, monounsaturated, polyunsaturated fatty acids, and any combination thereof. According to additional embodiments, the $C_{14}$-$C_{18}$ fatty acids are selected from the group consisting of myristic acid (14:0), palmitic acid (16:0), palmitoleic acid (16:1), stearic acid (18:0), oleic acid (18:1 ω-9), linoleic acid (18:2 ω-6), alpha linolenic acid (18:3 ω-3), and any combination thereof.

According to other embodiments, the $C_{20}$-$C_{22}$ fatty acids are selected from the group consisting of arachidonic acid (AA; 20:4 ω-6), eicosapentaenoic acid (EPA; 20:5 ω-3), docosahexaenoic acid (DHA; 22:6 ω-3), and any combination thereof.

According to another aspect, the present invention provides a parenteral nutrition emulsion composition comprising a structured triglyceride, the structured triglyceride comprises a glycerol backbone having three fatty acid residues esterified thereto, wherein at least one fatty acid residue is selected from the group consisting of $C_6$-$C_{12}$ fatty acids and active derivatives thereof, and at least one fatty acid residue is selected from the group consisting of $C_{14}$-$C_{18}$ fatty acids, $C_{20}$-$C_{22}$ fatty acids, and active derivatives thereof, with the proviso that a $C_{18}$-$C_{22}$ ω-3 fatty acid residue is not present on the same glycerol backbone together with gamma linolenic acid or dihomogamma linolenic acid.

According to a further aspect, the present invention provides a parenteral nutrition emulsion composition comprising a structured triglyceride, the structured triglyceride comprises a glycerol backbone having three fatty acid residues esterified thereto, wherein at least one fatty acid residue is selected from the group consisting of $C_6$-$C_{12}$ fatty acids and active derivatives thereof in the internal position of the glycerol backbone, and at least one fatty acid residue is selected from the group consisting of $C_{14}$-$C_{18}$ fatty acids, $C_{20}$-$C_{22}$ fatty acids, and active derivatives thereof in an external position of the glycerol backbone.

According to some embodiments, the parenteral nutrition emulsion composition comprises from about 9 to about 90% $C_6$-$C_{12}$ fatty acids based on the weight of total fatty acids in the parenteral nutrition emulsion composition. According to additional embodiments, the parenteral nutrition emulsion composition comprises from about 30 to about 60% $C_6$-$C_{12}$ fatty acids based on the weight of total fatty acids in the parenteral nutrition emulsion composition. According to further embodiments, the parenteral nutrition emulsion composition comprises from about 40 to about 50% $C_6$-$C_{12}$ fatty acids based on the weight of total fatty acids in the parenteral nutrition emulsion composition. According to non-limiting exemplary embodiments, the parenteral nutrition emulsion composition comprises caproic acid (6:0), caprylic acid (8:0), capric acid (10:0), and lauric acid (12:0), which constitute, respectively, about 0-5%, about 20-30%, about 10-30%, and about 0-5% by weight of total fatty acids in the parenteral nutrition emulsion composition.

According to other embodiments, the parenteral nutrition emulsion composition comprises from about 9 to about 90% $C_{14}$-$C_{18}$ fatty acids based on the weight of total fatty acids in the parenteral nutrition emulsion composition. According to additional embodiments, the parenteral nutrition emulsion composition comprises from about 30 to about 70% $C_{14}$-$C_{18}$ fatty acids based on the weight of total fatty acids in the parenteral nutrition emulsion composition. According to additional embodiments, the parenteral nutrition emulsion composition comprises from about 35 to about 55% $C_{14}$-$C_{18}$ fatty acids based on the weight of total fatty acids. According to non-limiting exemplary embodiments, the parenteral nutrition emulsion composition comprises myristic acid, palmitic acid, palmitoleic acid, stearic acid, oleic acid, linoleic acid, and alpha linolenic acid, which constitute, respectively, about 0-5%, about 5-30%, about 0-5%, about 0-5%, about 10-30%, about 10-30% and about 5-15% by weight of total fatty acids in the parenteral nutrition emulsion composition.

According to additional embodiments, the parenteral nutrition emulsion composition comprises from about 1 to 20% $C_{20}$-$C_{22}$ fatty acids based on the weight of total fatty acids in the parenteral nutrition emulsion composition. According to some embodiments, the parenteral nutrition emulsion composition comprises from about 1 to about 10% $C_{20}$-$C_{22}$ fatty acids based on the weight of total fatty acids in the parenteral nutrition emulsion composition. According to non-limiting exemplary embodiments, the parenteral nutrition emulsion composition comprises AA, EPA, and DHA, which constitute, respectively, about 1-5%, about 0-5% and about 1-5% by weight based on the weight of total fatty acids in the parenteral nutrition emulsion composition. It will be understood that a combination of the fatty acids disclosed hereinabove in a parenteral nutrition emulsion is highly advantageous in order to provide the nutritional needs of preterm- and term-infants, children, adults, cancer patients, patients suffering from burns, and critically ill patients.

According to some embodiments, a majority of structured triglycerides of the parenteral nutrition emulsion compositions of the present invention have one fatty acid residue selected from the group consisting of $C_{14}$-$C_{18}$ fatty acids, $C_{20}$-$C_{22}$ fatty acids, and active derivatives thereof, and two fatty acid residues selected from the group consisting of $C_6$-$C_{12}$ fatty acids and active derivatives thereof. According to additional embodiments, the structured triglycerides having one fatty acid residue selected from the group consisting of $C_{14}$-$C_{18}$ fatty acids, $C_{20}$-$C_{22}$ fatty acids, and active derivatives thereof, and two fatty acid residues selected from the group consisting of $C_6$-$C_{12}$ fatty acids and active derivatives thereof comprise from about 80% to about 100% of total structured triglycerides of said emulsions.

According to other embodiments, the ratio of ω-6/ω-3 fatty acids in the parenteral nutrition emulsion composition ranges from about 7:1 to 1:1. According to additional embodiments, the ratio ranges from about 3:1 to about 1:1. According to an exemplary embodiment, the ratio of ω-6/ω-3 fatty acids in the parenteral nutrition emulsion composition ranges from about 2:1 to about 1.5:1. The present invention thus also encompasses ratio of ω-6 to ω-3 fatty acids of 1:1.

According to some embodiments, the parenteral nutrition emulsion compositions comprise from about 10 to about 40% (w/v) of the structured triglycerides of the invention. According to other embodiments, the parenteral nutrition emulsion compositions comprise from about 15 to about 30% (w/v) of the structured triglycerides of the invention. According to an exemplary embodiment, the parenteral nutrition emulsion compositions comprise about 20% (w/v) of the structured triglycerides of the invention.

According to additional embodiments, a droplet size of the parenteral nutrition emulsion compositions of the invention is lower than about 1 μm. According to some embodiments, the droplet size of the parenteral nutrition emulsion compositions of the invention is lower than about 0.45 μm. According to other embodiments, the droplet size is lower than about 0.22 μm. It will be understood that this droplet size enables filtering the emulsion through a membrane filter having a pore size of 0.22 μm, and thus achieves higher sterilization of the emulsions.

According to other embodiments, the parenteral nutrition emulsion composition further comprises vitamin E. According to some embodiments, the vitamin E is alpha tocopherol. The amount of the alpha tocopherol in a parenteral nutrition emulsion of the invention is from about 0.1 to about 5 mg per 1 g of fatty acids. Preferably, the amount of alpha tocopherol is from about 1 to about 2 mg per 1 g of fatty acids. According to an exemplary embodiment, the parenteral nutrition emulsion comprises 1.8-2.0 mg of alpha tocopherol per 1 g of fatty acids.

According to some embodiments, the parenteral nutrition emulsion composition further comprises an emulsifier. The amount of an emulsifier such as, for example phospholipids, in the parenteral nutrition emulsion composition is from about 0.5 to about 4% (w/v). According to additional embodiments, the amount of the emulsifier is from about 0.5 to about 2.5% (w/v). According to an exemplary embodiment, the parenteral nutrition emulsion composition comprises about 1-1.2% (w/v) of phospholipids.

According to other embodiments, the parenteral nutrition emulsion composition can further comprise an osmolality modifier. An example of an osmolality modifier is glycerin. The amount of an osmolality modifier can range from about 1 to about 5% (w/v).

The parenteral nutrition emulsion composition can further comprise at least one component selected from the group consisting of surfactants, carbohydrate nutrients, electrolytes, amino acids, vitamins, trace minerals, preservatives and water. The parenteral nutrition emulsion composition can also comprise sterile water.

According to certain non-limiting embodiments, the parenteral nutrition emulsion composition comprises:
(a) about 20% (w/v) structured triglycerides comprising:
about 40-50% by weight $C_6$-$C_{12}$ fatty acids based on the weight of total fatty acids, wherein the $C_6$-$C_{12}$ fatty acids comprise 0-5% caproic acid, 20-30% caprylic acid, 10-30% capric acid, and 0-5% lauric acid based on the weight of total fatty acids;
about 35-55% by weight $C_{14}$-$C_{18}$ fatty acids based on the weight of total fatty acids, wherein the $C_{14}$-$C_{18}$ fatty acids comprise 0-5% mystiric acid, 5-30% palmitic acid, 0-5% palmitoleic acid, 0-5% stearic acid, 10-30% oleic acid, 10-30% linoleic acid, and 5-15% alpha linolenic acid based on the weight of total fatty acids; and
about 4.5-5.5% by weight $C_{20}$-$C_{22}$ fatty acids based on the weight of total fatty acids, wherein the $C_{20}$-$C_{22}$ fatty acids comprise 1-5% AA, 0-5% EPA, and 1-5% DHA based on the weight of total fatty acids, wherein the ratio of ω-6 to ω-3 fatty acids is about 1:1-2:1;
(b) about 1.2% (w/v) phospholipids;
(c) about 1.8-2.0 mg/1 g of fatty acids alpha tocopherol;
(d) about 10-25 g/L glycerin; and
(e) water.

According to another exemplary embodiment, the parenteral nutrition emulsion composition comprises:
(a) about 20% (w/v) structured triglycerides comprising:
about 45% by weight $C_6$-$C_{12}$ fatty acids based on the weight of total fatty acids, wherein the $C_6$-$C_{12}$ fatty acids comprise 2.5% caproic acid, 30% caprylic acid, 10% capric acid, and 2.5% lauric acid by weight based on the weight of total fatty acids;
about 50% by weight $C_{14}$-$C_{18}$ fatty acids based on the weight of total fatty acids, wherein the $C_{14}$-$C_{18}$ fatty acids comprise 10% palmitic acid, 2.5% stearic acid, 15% oleic acid, 16% linoleic acid, and 7% alpha linolenic acid by weight based on the weight of total fatty acids; and
about 5% by weight $C_{20}$-$C_{22}$ fatty acids based on the weight of total fatty acids, wherein the $C_{20}$-$C_{22}$ fatty acids comprise 1.5% AA, 1.5% EPA, and 1.5% DHA by weight based on the weight of total fatty acids, wherein the ratio of ω-6 to ω-3 fatty acids is 1.75;
(b) about 1.2% (w/v) phospholipids;
(c) about 1.8 mg/1 g of fatty acids alpha tocopherol;
(d) about 10-25 g/L glycerin; and
(e) water.

According to a further aspect, the present invention provides a process of synthesizing a structured triglyceride of the invention comprising the step of performing an acidolysis reaction. According to some embodiments, the acidolysis reaction is catalyzed by a lipase. According to additional embodiments, the triglyceride is a medium chain triglyceride. According to additional embodiments, the fatty acid is selected from the group consisting of $C_{14}$-$C_{18}$ fatty acids, $C_{20}$-$C_{22}$ fatty acids, and active derivatives thereof. According to additional embodiments, the process of synthesizing the structured triglyceride of the invention further comprises the step of distilling the reaction mixture to remove non-reacted MCT and fatty acid.

According to another aspect, the present invention provides a process of preparing a parenteral nutrition emulsion composition comprising the step of reducing the droplet size of the emulsion below of about 1 μm. According to some embodiments, the droplet size is reduced below 0.45 μm. According to non-limiting exemplary embodiments, the droplet size is reduced below 0.22 μm.

According to another aspect, the present invention provides a method of providing nutrition to a subject in need thereof comprising parenterally administering to the subject a parenteral nutrition emulsion composition of the invention.

According to some embodiments, the subject to be nourished by the parenteral nutrition emulsion composition of the invention is a preterm infant, a term infant, a child, an adult, a critically ill patient, a cancer patient, or a patient suffering from surgical trauma, burns, malnutrition, starvation, aging, or immunosuppression. According to other embodiments, the subject to be nourished by the parenteral nutrition emulsion of the invention is a patient suffering from AIDS.

These and other embodiments of the present invention will be better understood in relation to the description, examples, and claims that follow.

BRIEF DESCRIPTION OF THE FIGURES

FIG. 2A, peak 1 represents the free fatty acid, namely palmitic acid while peaks 2, 3, 4 and 5 represent the MCT before the reaction and peak 6 is trilaurin, an internal standard. FIG. 2B, peaks 1, 2 and 3 represent the liberated medium-chain fatty acids, while peak 4 represents the non-reacted palmitic acid. Peaks 5, 6, 7 and 8 represent the non-reacted MCT in the reaction medium, while peaks 9, 10, and 11 represent the new products containing one long-chain fatty acyl group. Peaks 12 and 13 represent the new products containing two long-chain fatty acyl groups.

DETAILED DESCRIPTION OF THE INVENTION

Figure 1:
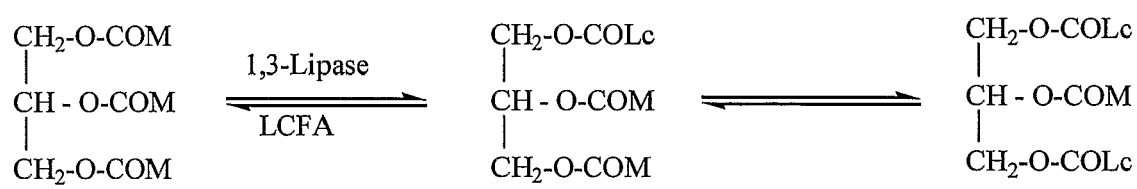
FIG. 1 shows a schematic presentation of the lipase-catalyzed acidolysis reaction between MCT and free fatty acids in solvent-free system. M represents medium-chain fatty acyl group and Lc represents long-chain or very long chain fatty acyl group.

The present invention provides structured triglycerides and parenteral nutrition emulsions comprising same useful in parenteral nutrition of preterm- and term-infants, children, adults, critically ill patients, and cancer patients.

According to one aspect, the present invention provides a structured triglyceride comprising a glycerol backbone having three fatty acid residues esterified thereto, wherein at least one fatty acid residue is selected from medium chain fatty acids and active derivatives thereof, and at least one fatty acid residue is selected from the group consisting of long chain fatty acids, very long chain fatty acids, and active derivatives thereof, with the proviso that a $C_{18-22}$ ω-3 fatty acid residue is not present on the same glycerol backbone together with gamma linolenic acid or dihomogamma linolenic acid.

The term "active derivatives" as used herein includes esters, ethers, amines, amides, substituted fatty acids (e.g., halogen substituted fatty acids), and other substitutions, which do not affect the beneficial properties of the fatty acids.

The term "ω-3", "ω-6" and "ω-9" as used herein refers to a fatty acid in which a double bond is present at the third carbon, sixth carbon, and ninth carbon, respectively, from the methyl end of the hydrocarbon chain. This nomenclature is equivalent to the n-3, n-6, and n-9 designations. Thus, the terms ω-3, ω3, and n-3; ω-6, ω6, and n-6; and 9, ω9, and n-9 are used interchangeably throughout the specification and claims of the present invention.

The structured triglycerides of the invention are made as "designer oils". Using enzymatic procedures known in the art that direct the incorporation of specific fatty acids to specific positions in the glycerol molecule, structured triglycerides are synthesized.

U.S. Pat. No. 6,537,787, the content of which is incorporated by reference as if fully set forth herein, discloses a method for obtaining a mixture enriched with polyunsaturated fatty acid triglycerides in the presence of a position-specific lipase, particularly 1,3-specific lipase. The specific lipase according to U.S. Pat. No. 6,537,787 is preferably a *Candida antarctica* lipase.

U.S. Pat. No. 6,518,049, the content of which is incorporated by reference as if fully set forth herein, discloses a process for esterifying a marine oil composition containing EPA and DHA as free fatty acids to form a free fatty acid fraction enriched in at least one of these fatty acids as compared to the starting composition, comprising the step of reacting the marine oil composition with glycerol in the presence of a lipase catalyst under reduced pressure and essentially organic solvent-free conditions, and recovering a free fatty acid fraction enriched in at least one of EPA and DHA. According to U.S. Pat. No. 6,518,049 the lipase is preferably immobilized on a carrier and is *Rhizomucor miehei* lipase.

Sugihara et al. (Appl. Microbiol. and Biotech. 1993 40:279-83 and references cited therein) disclosed a microorganism having a moderate selectivity towards the sn-2 position in glycerides. Ota et al. (Biosci. Biotechnol. Biochem. 2000, 64: 2497) disclosed an enzyme of *Geotrichum candidum*, which hydrolyzes the sn-2-positioned ester bond nearly twice more as compared to hydrolysis of the 1- or 3-positioned ester bonds.

U.S. Pat. No. 6,605,452 to Basheer, the content of which is incorporated by reference as if fully set forth herein, discloses a lipase preparation immobilized onto an insoluble matrix that preferably has 1,3-positional specificity with respect to triacylglycerols.

Thus, according to the principles of the present invention, a lipase can be used in a crude form, e.g., as supplied by a manufacturer or as isolated by any method known in the art for isolation of lipases, or a lipase or a surfactant-coated lipase complex can be immobilized on an insoluble matrix and subsequently used for preparing the structured triglycerides of the present invention. The lipase can be derived from any source, though a preferable source is a microorganism. Many different species can be used as a source of the lipase including, but not limited to, *Aspergillus niger, Aspergillus oryzae, Burkholderia* sp., *Candida antarctica* such as *Candida antarctica* A and B, *Candida cylindracea, Candida lipolytica, Candida rugosa, Chromobacterium viscosum, Humicola* sp., Lipoprotein lipase *Pseudomonas* A, *Mucor javanicus, Mucor miehei, Penicillium roqueforti, Pseudomonas fluorescens, Pseudomonas Cepacia, Porcine pancreatic* lipase (PPL), *Rhizopus arrhizus, Rhizopus javanicus, Rhizopus japonicus, Rhizopus oryzae, Rhizopus miehei,* and *Rhizopus niveus, Thermomyces lanuginose,* and Wheat germ lipase. The lipases used for the production of the structured triglycerides of the invention have 1,3-positional specificity with respect to the structured triglyceride.

Structured triglycerides of this invention can be prepared by various methods as are well known in the art. The structured triglycerides can be prepared by esterification of fatty acids and glycerol, acidolysis, transesterification and interesterification. In the specification and the claims that follow the term acidolysis includes reactions between one or more free fatty acid and a triglyceride to exchange at least one fatty acid of the triglyceride with at least one of the free fatty acids. According to some embodiments acidolysis is performed by reacting MCT and free fatty acids (i.e., reaction of the free fatty acids with MCT to exchange one or more of the MCFA). In the specification and the claims that follow the term transesterification includes reactions between two distinct triglycerides to exchange at least one fatty acid of the first triglyceride with at least one of the fatty acids of the second triglyceride. According to some embodiments transesterification is performed by reacting an MCT and an LCT. In the specification and the claims that follow the term interesterification includes reactions of a triglyceride with an alkyl ester of a fatty acid. According to some embodiments the interesterification reaction of the fatty acid alkyl ester is with an MCT to exchange one or more of the MCFA. The fatty acid alkyl ester is typically though not exclusively a methyl or ethyl fatty acid ester. According to some embodiments the reaction is catalyzed using a lipase preparation. It should also be noted that contacting a lipase preparation with fatty acid-containing substrates may be effected within a reaction reactor, e.g., a tank reactor or a fixed-bed reactor. It will be understood that any method known in the art for preparing the structured triglycerides is encompassed in the present invention.

Typically, the structured triglycerides of the invention can be prepared by acidolysis reaction between MCT and free fatty acids using lipases as supplied by the manufacturers or immobilized on an insoluble matrix. For immobilization of the lipases, an insoluble matrix, such as a silicate or an ion-exchange resin, is used and the lipases are immobilized from their aqueous solutions. Wet immobilized lipases are pretreated with a mixture of biphase medium containing phosphate buffer solution and oil and then dried under vacuum to reduce the water content of the immobilized lipase down to less than 2 wt %. Lipases can also be immobilized and activated according to procedures well known in the art. For example, immobilized and activated lipases possessing acidolysis activity can be prepared by attaching a polyethylene group to the surface functional group of the enzyme according to U.S. Pat. No. 4,645,741 to Inada et. al. Lipases can also be activated and immobilized according to the procedure described by Boosley et al. (U.S. Pat. No. 5,232,843) where a lipase is immobilized on a hydrophobic surface, e.g., silica or an ion-exchange resin, precoated with a non-lipase protein. Immobilized lipases on a dry, porous particulate hydrophobic support and containing a surfactant prepared according to U.S. Pat. No. 5,773,266 and U.S. Pat. No. 6,596,520, can also be applied for producing the structured triglycerides of the present invention.

Additionally or alternatively, other methods for preparing structured triglycerides of the present invention can involve the use of alkali metal catalysts such as sodium, and/or nucleophilic catalysts, such as hydroxides and alkoxides, which function to randomly exchange fatty acids on the glycerol backbone of the glycerol molecule.

Inclusion of $C_6$-$C_{12}$ fatty acids in the structured triglycerides has some benefits. The $C_6$-$C_{12}$ fatty acids do not need carnitine to enter the mitochondria, thus they are rapidly cleared from blood and are used as energy source. As a component of the structured triglycerides, MCFA contribute to achieve a lower molecular weight, better solubility and better stability of the emulsion.

According to another aspect, the present invention provides a parenteral nutrition emulsion comprising the structured triglyceride of the invention. It is apparent to a person skilled in the art that the present invention encompasses nutrition emulsions comprising the structured triglycerides of the invention for enteral nutrition.

According to some embodiments, the parenteral nutrition emulsion further comprises vitamin E, preferably alpha tocopherol. The normal range of plasma tocopherol concentrations is between 0.7 and 1.6 mg/100 ml. Generally, the recommended amount of vitamin E for premature infants is 4.55 mg/day and for adults it is 100-200 mg/day. Vitamin E is classified as a practically non-toxic substance. A dosage below 1000 mg/day is safe and free from side effects. In order to maintain normal range of tocopherol, vitamin E should be matched quantitatively to unsaturated FA. Therefore, the parenteral nutrition emulsion of the invention can comprise 0.1 to 5 mg of alpha tocopherol per 1 g of fatty acids. Preferably, the parenteral nutrition emulsion can comprise 1 to 2 mg of alpha tocopherol per 1 g of fatty acids.

The parenteral nutrition emulsion composition according to the invention can advantageously further comprise a natural biologically compatible emulsifier. The emulsifier is preferably a phospholipid compound or a mixture of phospholipids, such as lecithin, phosphatidylcholine, phosphatidyl ethanolamine or mixtures thereof. Non-limiting examples of phospholipids which can be used in the compositions of the invention are lecithins; EPIKURON 170® being a mixture of about 70% (w/v) of phosphatidylcholine, 12% phosphatidylethanolamine, and about 16% other phospholipids, or OVOTHIN 160® being a mixture comprising about 60% (w/v) phosphatidylcholine, 18% (w/v) phosphatidylethanolamine, and 12% (w/v) other phospholipids, both manufactured by Lucas Meyer (Germany). These mixtures of mainly phosphatidylcholine and phosphatidylethanolamine are derived from a natural source, such as purified egg yolk phospholipids (for the Ovothin series) and soybean oil phospholipids (for the Epikuron series); a purified phospholipid mixture; LIPOID E-80® being a phospholipid mixture comprising about 80% (w/v) phosphatidylcholine, about 8% (w/v) phosphatidylethanolamine, about 3.6% non-polar lipids, and about 2% sphingomyeline, manufactured by Lipoid KG (Ludwigshafen, FRG). Other phospholipids of plants (e.g., lecithin) or of animal origin known in the art can be used as emulsifiers for the preparations of the parenteral nutrition emulsion compositions of the invention. For example, other forms of emulsifiers containing fatty acyl groups, such as polyol fatty acid esters, can be used for the preparations of such emulsions.

The emulsion can further comprise a pharmaceutically acceptable non-natural surfactant. Any conventional pharmaceutically acceptable non-ionic surfactant can be used. Generally, the surfactant is a non-ionic alkylene oxide condensate of an organic compound, which contains one or more hydroxyl groups. For example, ethoxylated and/or propoxylated alcohol or ester compounds or mixtures thereof are commonly available and are well known to those skilled in the art. Suitable surfactants include, but are not limited to, TYLOXAPOL; POLOXAMER 4070; POLOXAMER 188; POLYOXYL 40 Stearate; POLYSORBATE 80, and POLYSORBATE 20, as well as various compounds sold under the trade name TWEEN (ICI American Inc., Wilmington, Del., U.S.A.), PLURONIC F-68 (trade name of BASF, Ludwigshafen, Germany for a copolymer of polyoxyethylene and polyoxypropylene). Preferred surfactants also include polyoxyethylated oils or poloxamines. The TYLOXAPOL and TWEEN surfactants are most preferred because they are FDA approved for human use.

The parenteral nutrition emulsion composition can further comprise carbohydrate nutrients such as, for example, dextrose; electrolytes such as, for example, potassium and sodium chloride; amino acids including essential and non-essential amino acids; vitamins such as, for example, vitamin A, and vitamin D; trace minerals such as, for example, zinc ions; and a preservative such as, for example, methyl-, ethyl-, propyl-, and butylparaben, which are medically accepted for parenteral administration.

The parenteral nutrition emulsion composition can further comprise an osmolality modifier such as glycerin, sorbitol, or alanine (see, for example, U.S. Pat. No. 4,567,045, the content of which is incorporated by reference as if fully set forth herein), and sterile water.

Generally, lipid droplets in emulsions for medical use should preferably be small, i.e., below about 1 µm, since the smaller the droplets, the more stable the emulsion is in storage. The droplet size is advantageously in the size range of about 0.05 to 0.5 µm, and preferably about 0.1 to 0.3 µm. The droplet size is of particular importance since large droplets will not readily pass through small blood capillaries and will not pass through a filter required for filtration of the emulsion before its administration to a subject in need thereof. The compositions of the invention are particularly suitable for obtaining such small droplets.

The emulsions of the present invention can be prepared by a number of ways. In accordance with one preparation method, an aqueous solution and an oily solution are separately prepared, the aqueous solution comprising the phospholipids and optionally also an osmotic pressure regulator and a preservative, and the oily solution comprising the structured triglycerides, and an antioxidant. The aqueous solution is prepared from two premade solutions: a first, alcoholic solution containing the phospholipids and a second solution containing the other optional ingredients mentioned above in water. The aqueous solution is then prepared by mixing the first and the second solutions, and removing the alcohol, for example by evaporation, to yield the aforementioned aqueous solution.

The aqueous solution and the oily solution are then mixed with one another. However, the so-obtained mixture does not yet consist of sufficiently small droplets, the size of which (obtained after mixing with a magnetic stirrer) is about 10 µm. The droplet size of the inventive emulsion can then be decreased by the use of emulsification equipment such as UltraTurrax (Jankl and Kunkel, Staufen, FRG), which yields droplets having an average diameter of about 1.1 µm, or of a high shear mixer, e.g., Polytron (Kinematica, Lucerne, Switzerland), which yields droplets having an average diameter of about 0.65 µm.

Especially small droplets can be obtained in the inventive emulsions by utilizing a two-stage pressure homogenizer in which the crude dispersion is forced under high pressure through the angular space between a spring loaded valve and the valve seat, the second stage being in tandem with the first so that the emulsion is subjected to two very rapid dispersion processes. An example of such an apparatus is the Gaulin Homogenizer (APV Gaulin, Hilversum, The Netherlands). Use of such an apparatus in accordance with the invention yields emulsions in which the droplets have an average diameter of about 0.27 µm with a relatively small deviation.

Even smaller droplets can be obtained when the emulsification process combines the use of both a Polytron-type high shear mixer followed by homogenization. The droplet size, which is obtained in such a combination, is about 0.1-0.15 µm. These relatively small size droplets are preferred when the emulsion is to be used for intravenous administration or when the formulation is to be sterilized by filtration.

According to some embodiments, the emulsions of the present application are prepared by applying a high shear mixer (Ultraturrax) for 5 min at a mixing rate of 10,000 RPM. Emulsions obtained after this stage are further treated with a microfluidizer at a pressure typically in the range of 800-2600 bar for five minutes at room temperature. Thereafter, the emulsions are cooled to room temperature and the mean droplet size is lower than 0.2 µm. Emulsions obtained after the aforementioned two-stage process are sterilized by filtration using a membrane filter having a pore size of less than 0.45 µm, and preferably less than 0.2 µm. The pH in the emulsion is adjusted to a physiologically accepted pH, typically pH of 6 to 8, with 0.5M NaOH or 0.5 M HCl solutions.

Another method for preparing the parenteral nutrition emulsion compositions of the invention is by mixing together a liposome mixture and an oily mixture, each one prepared separately beforehand. The liposome mixture comprises all the ingredients, which in the final composition do not form part of the oily phase, namely the phospholipids, and also the optional osmotic pressure regulator and the preservative. The preparation of the liposome mixture from these ingredients can be carried out by means known in the art.

The oily mixture comprises the structured triglycerides, and also the anti-oxidant.

After the liposome mixture is mixed together with the oily mixture, an emulsion is formed having relatively large droplets, e.g., about 10 µm, which is further processed in a similar manner as described above in connection with the first preparation method, until an emulsion having fine homogenous droplets is obtained.

Typically, the emulsions of the present invention are filtered through a membrane filter having a pore size of less than 0.45 µm, preferably a membrane filter having a pore size of 0.2 µm. The emulsions are further sterilized by heating up to 121° C. for 15 min under inert gas atmosphere such as, for example, nitrogen, while rotating the emulsion during autoclaving. However, any method for sterilization as known in the art is encompassed in the present invention.

Distillation of the structured triglycerides is performed by heating and evaporating the structured triglycerides, preferably under vacuum. Preferably, the structured triglycerides of the present invention are subjected to molecular or short-path distillation, which is performed at low temperature under very low pressure, typically below 0.01 mm Hg. Preferably, the distillation is conducted at a temperature of 120° C. to 230° C. The pressure can vary from about $1 \times 10^{-3}$ kPa to 0.533 kPa. This low pressure enables the separation of high molecular weight compounds such as the structured triglycerides of the invention. Free fatty acids can also be removed from the reaction mixture by washing with a sodium hydroxide or an alkoxide solution, preferably of about 0.5M. Alternatively or additionally, the free fatty acid can also be removed from the reaction mixture by steam stripping.

The emulsions of the present invention are packaged and stored in hermetically sealed containers for long or short-term storage. The additives to be included in the emulsions will depend upon how long the emulsions are to be stored. Long-term storage is acceptable for emulsions with aqueous phases containing sugar, the amino acids and some electrolytes. Dextrose should not be included in emulsions prepared for long-term storage.

Advantages of Different Classes of Fatty Acids

The group of medium chain fatty acids (MCFA) includes fatty acids that consist of 6-12 carbon atoms. Their chemical and physical structure makes the MCFA more soluble than long or very long chain fatty acids (LCFA or VLCFA, respectively); the latter terms denote fatty acid of 14-18 and 20-22 carbon atoms, respectively. All the fatty acids in the MCFA group are saturated. Being rapidly oxidized, MCFA are considered as a very good source of energy.

Emulsions containing medium chain triglycerides (MCT) are more stable than those containing pure long chain triglycerides (LCT). As MCT enter the blood stream, lipases cleave the triglycerides hydrolytically to glycerol and free fatty acids. Since MCFA do not need carnitine to enter the mitochondria, the bulk of FA released is immediately taken up by the tissues and rapidly oxidized. This metabolic pathway enables MCFA to be eliminated from the blood stream more quickly than LCFA, and as such they do not increase blood triglyceride levels and they have low tendency of incorporation into tissue lipids. MCFA are also known to preserve body protein, to increase nitrogen retention, to decrease gluconeogenesis, and to improve nitrogen balance. MCFA are, therefore, used as a rapid energy source.

LCFA consist of 14-18 carbon atoms. They can be saturated, monounsaturated or polyunsaturated. Long chain triglycerides are transported in the blood as lipoproteins. Lipoprotein lipase and hepatic lipase hydrolyze LCT to FA and glycerol. The clearance of LCT from the blood is slower than MCT. LCFA enter the mitochondria by carnitine. LCFA function as an energy source by beta oxidation, as precursors of longer chain FA, and as a storage in adipose tissues. The most important LCFA are linoleic acid (18:2 ω-6) and alpha linolenic (18:3 ω-3), both considered essential FA since they cannot be synthesized by the human body, and therefore must be provided in the diet.

The group of very long chain fatty acids (VLCFA) includes chains of 20 carbon atoms or more. Most of the VLCFA are polyunsaturated. They are synthesized from LCFA by elongation process, which involves several enzymes. Among the most important VLCFA are arachidonic acid (AA), an ω-6 fatty acid, and docosahexaenoic (DHA), an ω-3 fatty acid, which have been shown to be necessary for normal development and function of the brain, the central nervous system (CNS) and the retina. AA and DHA are not only mechanical components of the CNS structure, but also required for cell signaling systems in neurons. There is evidence linking DHA deficiency to attention deficit and hyperactivity disorders, dyslexia, senile dementia, reduced visual and cognitive function, clinical depression, schizophrenia and other problems of psychological and physiological nature. In addition, eicosapentaenoic acid (EPA) and DHA, both ω-3 fatty acids, have been indicated to have beneficial effects on coronary heart disease, hypertension, inflammation, arthritis, psoriasis, and other autoimmune disorders and cancer. DHA and AA are also involved in the synthesis of prostaglandins, thromboxanes and leukotrienes. In addition, DHA and AA are crucial components of biological cell membranes. It has been well established that fetus, preterm and term infants require these fatty acids for their normal development.

Incorporation rates of DHA and AA in red blood cell membranes of infants were shown to decline without supplementation of DHA and AA. Infants fed with human milk (which contains DHA and AA) or formula supplemented with those fatty acids, were shown to maintain normal rates of incorporation. Other studies show that term and preterm infants fed with formula containing VLCFA exhibit better cognitive behavior and psychomotor development than term and preterm infants fed with formula that did not contain VLCFA.

The effect of ω-3 VLCFA, like DHA and EPA, on the immune system has been studied in animals and humans. Surgical patients that were given parenteral nutrition including DHA and EPA showed a rise in interleukin 2. Patients having inflammatory bowel diseases who received parenteral or enteral nutrition containing DHA and EPA, showed an improvement in their clinical state with a reduction of the steroid intake. These beneficial effects of VLCFA ω-3 on inflammatory diseases is presumably due to their involvement in interleukin production, which suppress inflammatory processes.

The VLCFA ω-3 have also been shown to exert beneficial effect on coronary heart diseases as they reduce platelet aggregation and blood viscosity, increase capillary flow, and reduce the risk of myocardial infarction. It should be appreciated that the rate of conversion of these very long chain fatty acids from their precursors is not adequate to fulfill the body requirements, and therefore such fatty acids have to be included in parenteral nutrition.

According to the principles of the present invention, at least part of the triglycerides incorporated into the parenteral nutrition emulsion comprise ω-6 fatty acids. It will be appreciated that among the ω-6 VLCFA, AA is one of the more preferred ω-6 fatty acids. According to the principles of the present invention, although the structured triglycerides can comprise any ω-6 fatty acid, gamma linolenic acid and dihomogamma linolenic acid are not present simultaneously on the same glycerol backbone with $C_{18-22}$ n-3 fatty acid residue.

Vitamin E

Vitamin E is the nutritional designation of the tocopherols, a group of essential biologically active substances. The various tocopherols are found in germinal cells of plants, in egg yolk, and in meat. The natural tocopherols include four isomers: alpha, beta, gamma, and delta. The most biologically active vitamin E is the alpha tocopherol isomer.

Consumption of fatty acids containing double bonds increases the hazard of peroxide formation, which leads to structural changes within cellular membranes. These changes are demonstrated particularly in impairment of the immune system function, in pulmonary complications, and in increased hemolysis.

Preterm infants and critically ill patients are more vulnerable to peroxidation hazards. Vitamin E is a highly effective antioxidant, protecting the double bonds of unsaturated fatty acids from oxidative destruction. This protective function is demonstrated both in vitro, in lipid emulsions, and in vivo, by protecting the lipid fracture of membranes.

Vitamin E is also essential for the maintenance of a functional immune system. In vitamin E deficiency there is a decrease in the resistance to infection, in the immune response, in the activation of T lymphocytes, in the production of interleukin 2, and in the phagocytic capacity. Patients receiving lipid emulsion in parenteral nutrition have an increased requirement for vitamin E.

The following examples are to be considered merely as illustrative and non-limiting in nature. It will be apparent to one skilled in the art to which the present invention pertains that many modifications, permutations, and variations may be made without departing from the scope of the invention.

Example 1

Identification of Lipases Suitable for Synthesis of Structured Triglycerides

Materials and Methods

MCT solution was purchased from (Croda, Singapore). The MCT solution contained 58% Caprylic acid and 42% Capric acid. According to the manufacturer, both fatty acids are distributed randomly on the glycerol backbone. Free fatty acids of different purities were purchased from Sigma. DHA and EPA were obtained from K. D. Pharma, Germany. Arachidonic acid bound to glycerol in a form of triglycerides was obtained from Martek, USA, at a concentration of 20%. All solvents and chemicals were obtained from Sigma and were of analytical grade. Lipases were purchased from Sigma, USA.

Acidolysis Reaction

The acidolysis activity of crude enzymes and enzymes adapted for synthetic reactions was assayed by adding an enzyme preparation (500 mg) into a 10 ml reaction solution containing MCT and a free fatty acid where the molar ratio between both substrates was 1:1. The reaction mixture was shaken for 16 hours at a temperature of 50° C. Samples (0.1 ml) were taken from the reaction mixture and mixed with 10 ml solvent comprised of acetone-dichloromethane at a ratio of 90:10. The samples were filtered through a Millipore filter (pore size 0.45 μm) and then injected to the HPLC. The reaction is presented in FIG. 1.

Analysis

The reaction progress was followed by analyzing the triglyceride composition in the reaction medium before and after the enzymatic reaction using an HPLC equipped with an ELSD (Evaporative light Scattering Detector). The HPLC was equipped with a LiChrosorb CH-18 Super (250×4 mm, 5 μm, MERCK). The HPLC running conditions were as follows: mobile phase A, Acetonitrile/Dichloromethane/Acetone (80/15/5); mobile phase B: Acetone/Dichloromethane/Acetone (20/60/20). The flow rate was 1 ml/min and the gradient was 0 to 100% B for 30 min.

Figure 2A:
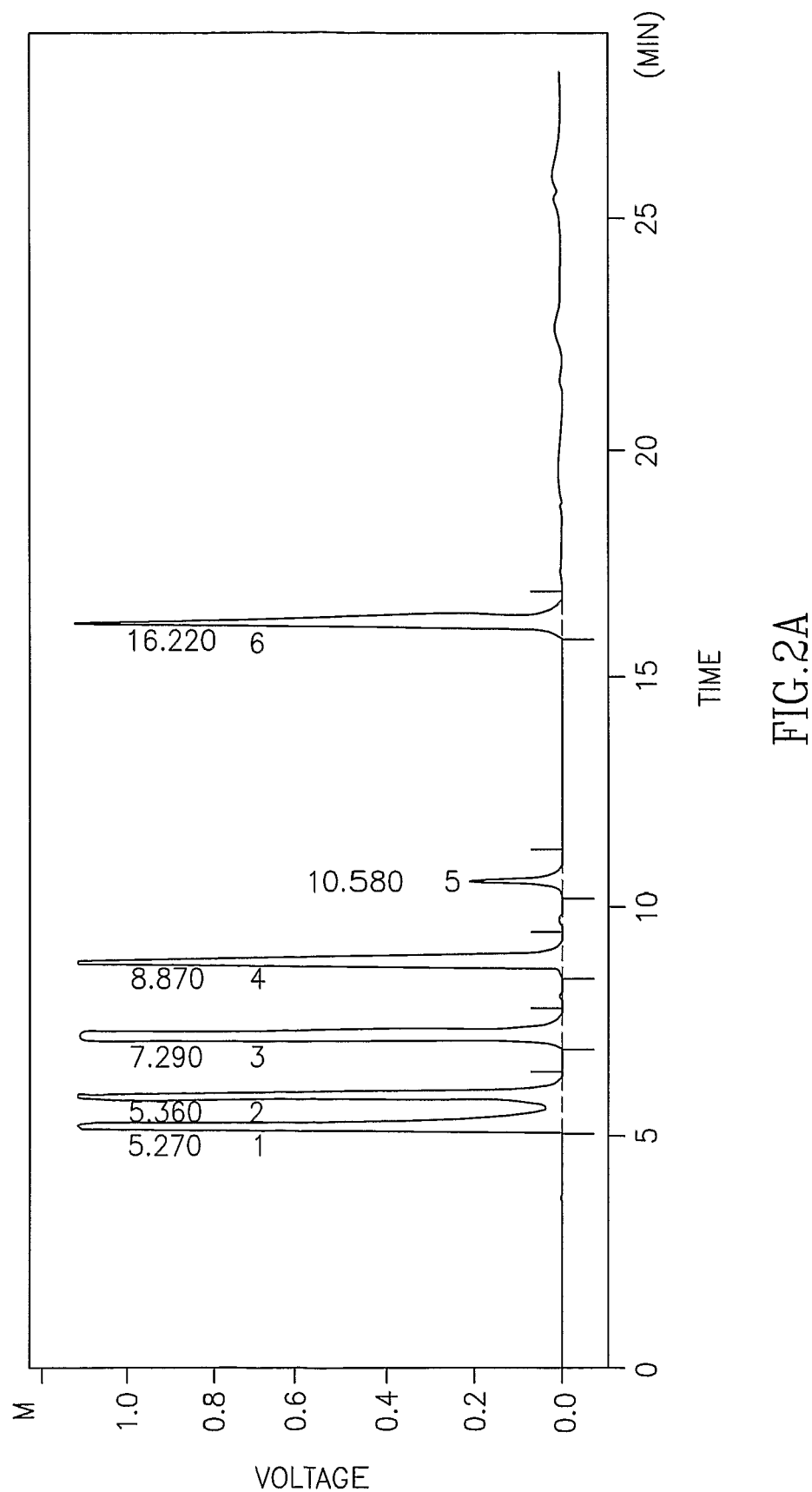
FIGS. 2A-B show HPLC chromatograms of MCT before and after an acidolysis reaction.
Figure 2B:
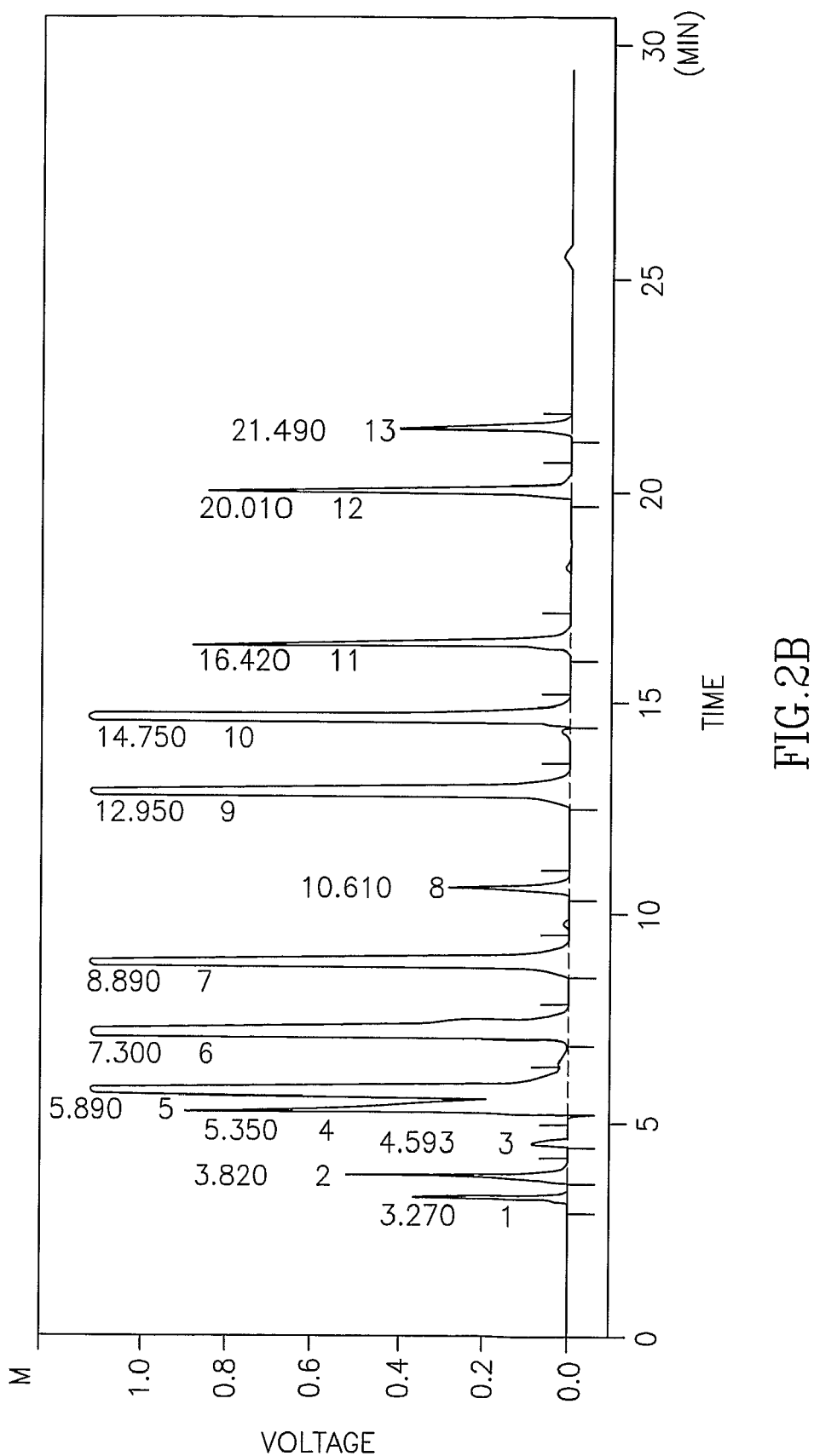

FIGS. 2A and 2B show HPLC chromatograms before and after acidolysis reaction of MCT. FIG. 2A, peak 1 represents the free fatty acid, namely palmitic acid while peaks 2, 3, 4 and 5 represent the MCT before the reaction and peak 6 is trilaurin, an internal standard. FIG. 2B, peaks 1, 2 and 3 represent the liberated medium-chain fatty acids, while peak 4 represents the non-reacted palmitic acid. Peaks 5, 6, 7 and 8 represent the non-reacted MCT in the reaction medium, while peaks 9, 10, and 11 represent the new products containing one long-chain fatty acyl group. Peaks 12 and 13 represent the new products containing two long-chain fatty acyl groups.

The substrate conversion was calculated as follows:

Conversion %=100×(Sum of area of the 4 peaks representing the MCT at time zero)−(Sum of area of the 4 peaks representing the MCT after 16 h reaction time)per Sum of area of the 4 peaks representing the MCT at time zero.

The MCT conversion (%) was used as an indicative parameter for the efficiency of enzyme activity to obtain the desired product.

Results

Tables 1-12 show the acidolysis activity of various lipases, which were screened for their ability to catalyze the reaction between MCT and free fatty acids in a solvent-free system according to the enzymatically catalyzed reaction presented in FIG. 1. All lipases were used in their crude form as supplied by the manufacturer (Sigma) or immobilized on an insoluble matrix. Immobilized lipases were activated before their use in the acidolysis reaction containing MCT and a long-chain fatty acid by pretreatment with a biphase system containing 50% triglyceride oil such as olive oil, soy oil and the like and 50% water. This pretreatment lead to the activation of the immobilized enzymes for synthetic applications.

A typical enzyme activation and immobilization procedure used in this example is as follows: 1 g of a crude lipase preparation was dissolved in a 1 L of phosphate buffer solution of an appropriate pH according to the recommendation of the enzyme's manufacturer. 10 g of support matrix (silica, celite, an ion-exchange resin such as DUOLITE® A56, DUOLITE® A7, DUOLITE® XAD761, or Amberlite™ XAD16) were added into the stirred enzyme solution. The slurry was shaken for 8 hours at a temperature of 10° C. Hundred ml of cold acetone was optionally added into the stirred slurry in order to enhance the enzyme immobilization on the matrix surface. The immobilized enzyme was filtered of from the mixture and then freeze-dried or used wet for the following step. One g of freeze-dried immobilized lipase (water content of less than 2 weight %) or wet immobilized lipase (water content of approx. 20%) was added into a biphase system comprised of 5 g olive oil and 2 g buffer solution of pH7 at room temperature. The mixture was stirred for 10 min. The immobilized lipases was filtered of from the mixture, washed with cold acetone, dried in a desiccator and then used for the acidolysis reaction between MCT and a fatty acyl donor.

TABLE 1

The acidolysis activity of different enzymes using MCT and caproic acid.

| Lipase origin | Conversion % (24 h) |
|---|---|
| *Aspergillus niger* | 5 |
| *Candida Antarctica* | 30 |
| *Candida cylindracea* | 2 |
| *Mucor miehei* | 35 |
| *Pseudomonas fluorescens* | 4 |
| *Pseudomonas cepacia* | 27 |
| *Rhizopus arrhizus* | 42 |
| *Rhizopus niveus* | 3 |
| Porcine pancreas lipase | 6 |
| *Aspergillus oryzae* | 8 |
| *Candida lipolytica* | 8 |
| *Mucor javanicus* | 32 |
| *Penicillium roqueforti* | 3 |
| *Rhizomucor miehei* | 31 |
| Wheat germ | 2 |
| *Chromobacterium viscosum* | 18 |
| Lipoprotein lipase *Pseudomonas* A | 17 |
| Lipoprotein lipase *Pseudomonas* B | 18 |

Reaction conditions: MCT (1 gr), caproic acid (0.23 gr), and 500 mg enzyme preparation. The reaction mixture was shaken and thermostated at 50° C. for 16 h.

The results presented in Table 1 show that there are 6 different preferred sources for lipases for the acidolysis reaction of Caproic acid and MCT. These sources of lipases include *Candida Antarctica, Mucor miehei, Pseudomonas cepacia, Rhizopus arrhizus, Mucor javanicus* and *Rhizomucor miehei*. Other lipases extracted form different sources of microorganisms did not show adequate acidolysis activity in organic medium.

TABLE 2

The acidolysis activity of different enzymes using MCT and Caprylic acid.

| Lipase origin | Conversion % (24 h) |
|---|---|
| *Aspergillus niger* | 3 |
| *Candida Antarctica* | 34 |
| *Candida cylindracea* | 5 |
| *Mucor miehei* | 42 |
| *Pseudomonas fluorescens* | 6 |
| *Pseudomonas cepacia* | 32 |
| *Rhizopus arrhizus* | 38 |
| *Rhizopus niveus* | 2 |
| Porcine pancreas lipase | 5 |
| *Aspergillus oryzae* | 9 |
| *Candida lipolytica* | 3 |
| *Mucor javanicus* | 37 |
| *Penicillium roqueforti* | 5 |
| *Rhizomucor miehei* | 37 |
| Wheat germ | 6 |
| *Chromobacterium viscosum* | 28 |
| Lipoprotein lipase *Pseudomonas* A | 15 |
| Lipoprotein lipase *Pseudomonas* B | 24 |

Reaction conditions were as described in Table 1, with one modification, namely caprylic acid (0.28 gr) was used as the fatty acid.

Table 2 shows that lipases extracted from *Candida Antarctica, Mucor miehei, Pseudomonas Cepacia, Rhizopus arrhizus, Mucor javanicus, Rhizomucor miehei, Chromobacte-*

*rium viscosum* and Lipoprotein lipase *Pseudomonas* A show reasonable acidolysis activity using Caprylic acid and MCT as starting materials.

Tables 3-9 herein below also show that the most active lipases to catalyze the reaction between MCT and FFA include mainly the enzymes extracted from the aforementioned group of microorganisms. These results indicate that such lipases are efficient for acidolysis reactions where the substrates are MCT and FFA providing that the fatty acid is saturated, mono-unsaturated, di-unsaturated or tri-unsaturated and consists of 6-18 carbons.

TABLE 3

The acidolysis activity of different enzymes using MCT and Capric acid.

| Lipase origin | Conversion % (24 h) |
|---|---|
| *Aspergillus niger* | 3 |
| *Candida Antarctica* | 25 |
| *Candida cylindracea* | 8 |
| *Mucor miehei* | 39 |
| *Pseudomonas fluorescens* | 9 |
| *Pseudomonas cepacia* | 37 |
| *Rhizopus arrhizus* | 42 |
| *Rhizopus niveus* | 3 |
| Porcine pancreas lipase | 5 |
| *Aspergillus oryzae* | 15 |
| *Candida lipolytica* | 5 |
| *Mucor javanicus* | 37 |
| *Penicillium roqueforti* | 5 |
| *Rhizomucor miehei* | 37 |
| Wheat germ | 6 |
| *Chromobacterium viscosum* | 28 |
| Lipoprotein lipase *Pseudomonas* A | 15 |
| Lipoprotein lipase *Pseudomonas* B | 24 |

Reaction conditions as described in Table 1, with one modification, namely capric acid (0.34 gr) was used as the fatty acid.

TABLE 4

The acidolysis activity of different enzymes using MCT and Laurie acid.

| Lipase origin | Conversion % (24 h) |
|---|---|
| *Aspergillus niger* | 5 |
| *Candida Antarctica* | 14 |
| *Candida cylindracea* | 2 |
| *Mucor miehei* | 38 |
| *Pseudomonas fluorescens* | 12 |
| *Pseudomonas cepacia* | 17 |
| *Rhizopus arrhizus* | 29 |
| *Rhizopus niveus* | 5 |
| Porcine pancreas lipase | 6 |
| *Aspergillus oryzae* | 14 |
| *Candida lipolytica* | 8 |
| *Mucor javanicus* | 41 |
| *Penicillium roqueforti* | 7 |
| *Rhizomucor miehei* | 39 |
| Wheat germ | 4 |
| *Chromobacterium viscosum* | 31 |
| Lipoprotein lipase *Pseudomonas* A | 17 |
| Lipoprotein lipase *Pseudomonas* B | 27 |

Reaction conditions as described in Table 1, with one modification, namely lauric acid (0.4 gr) was used as the fatty acid.

TABLE 5

The acidolysis activity of different enzymes using MCT and Palmitic acid.

| Lipase origin | Conversion % (24 h) |
|---|---|
| *Aspergillus niger* | 3 |
| *Candida Antarctica* | 22 |
| *Candida cylindracea* | 6 |
| *Mucor miehei* | 41 |
| *Pseudomonas fluorescens* | 2 |
| *Pseudomonas cepacia* | 31 |
| *Rhizopus arrhizus* | 39 |
| *Rhizopus niveus* | 1 |
| Porcine pancreas lipase | 1 |
| *Aspergillus oryzae* | 15 |
| *Candida lipolytica* | 5 |
| *Mucor javanicus* | 40 |
| *Penicillium roqueforti* | 2 |
| *Rhizomucor miehei* | 33 |
| Wheat germ | 2 |
| *Chromobacterium viscosum* | 31 |
| Lipoprotein lipase *Pseudomonas* A | 15 |
| Lipoprotein lipase *Pseudomonas* B | 26 |

Reaction conditions as described in Table 1, with one modification, namely palmitic acid (0.51 gr) was used as the fatty acid.

TABLE 6

The acidolysis activity of different enzymes using MCT and Stearic acid.

| Lipase origin | Conversion % (24 h) |
|---|---|
| *Aspergillus niger* | 3 |
| *Candida Antarctica* | 34 |
| *Candida cylindracea* | 5 |
| *Mucor miehei* | 42 |
| *Pseudomonas fluorescens* | 6 |
| *Pseudomonas cepacia* | 32 |
| *Rhizopus arrhizus* | 38 |
| *Rhizopus niveus* | 2 |
| Porcine pancreas lipase | 5 |
| *Aspergillus oryzae* | 9 |
| *Candida lipolytica* | 3 |
| *Mucor javanicus* | 37 |
| *Penicillium roqueforti* | 5 |
| *Rhizomucor miehei* | 37 |
| Wheat germ | 6 |
| *Chromobacterium viscosum* | 28 |
| Lipoprotein lipase *Pseudomonas* A | 15 |
| Lipoprotein lipase *Pseudomonas* B | 30 |

Reaction conditions as described in Table 1, with one modification, namely stearic acid (0.56 gr) was used as the fatty acid.

TABLE 7

The acidolysis activity of different enzymes using MCT and Oleic acid.

| Lipase origin | Conversion % (24 h) |
|---|---|
| *Aspergillus niger* | 1 |
| *Candida Antarctica* | 20 |
| *Candida cylindracea* | 3 |
| *Mucor miehei* | 40 |
| *Pseudomonas fluorescens* | 3 |
| *Pseudomonas cepacia* | 37 |
| *Rhizopus arrhizus* | 41 |
| *Rhizopus niveus* | 1 |
| Porcine pancreas lipase | 4 |
| *Aspergillus oryzae* | 12 |
| *Candida lipolytica* | 1 |

TABLE 7-continued

The acidolysis activity of different enzymes using MCT and Oleic acid.

| Lipase origin | Conversion % (24 h) |
| --- | --- |
| *Mucor javanicus* | 42 |
| *Penicillium roqueforti* | 2 |
| *Rhizomucor miehei* | 43 |
| Wheat germ | 2 |
| *Chromobacterium viscosum* | 33 |
| Lipoprotein lipase *Pseudomonas* A | 17 |
| Lipoprotein lipase *Pseudomonas* B | 29 |

Reaction conditions as described in Table 1, with one modification, namely, oleic acid (0.56 gr) was used as the fatty acid.

TABLE 8

The acidolysis activity of different enzymes using MCT and Linoleic acid.

| Lipase origin | Conversion % (24 h) |
| --- | --- |
| *Aspergillus niger* | 2 |
| *Candida Antarctica* | 19 |
| *Candida cylindracea* | 2 |
| *Mucor miehei* | 41 |
| *Pseudomonas fluorescens* | 3 |
| *Pseudomonas cepacia* | 37 |
| *Rhizopus arrhizus* | 42 |
| *Rhizopus niveus* | 4 |
| Porcine pancreas lipase | 5 |
| *Aspergillus oryzae* | 17 |
| *Candida lipolytica* | 2 |
| *Mucor javanicus* | 33 |
| *Penicillium roqueforti* | 3 |
| *Rhizomucor miehei* | 35 |
| Wheat germ | 4 |
| *Chromobacterium viscosum* | 20 |
| Lipoprotein lipase *Pseudomonas* A | 12 |
| Lipoprotein lipase *Pseudomonas* B | 17 |

Reaction conditions as described in Table 1, with one modification, namely linoleic acid (0.55 gr) was used as the fatty acid.

TABLE 9

The acidolysis activity of different enzymes using MCT and alpha-Linolenic acid.

| Lipase origin | Conversion % (24 h) |
| --- | --- |
| *Aspergillus niger* | 1 |
| *Candida Antarctica* | 15 |
| *Candida cylindracea* | 2 |
| *Mucor miehei* | 31 |
| *Pseudomonas fluorescens* | 2 |
| *Pseudomonas cepacia* | 35 |
| *Rhizopus arrhizus* | 37 |
| *Rhizopus niveus* | 1 |
| Porcine pancreas lipase | 6 |
| *Aspergillus oryzae* | 12 |
| *Candida lipolytica* | 2 |
| *Mucor javanicus* | 22 |
| *Penicillium roqueforti* | 3 |
| *Rhizomucor miehei* | 39 |
| Wheat germ | 3 |
| *Chromobacterium viscosum* | 15 |
| Lipoprotein lipase *Pseudomonas* A | 13 |
| Lipoprotein lipase *Pseudomonas* B | 12 |

Reaction conditions as described in Table 1, with one modification, namely alpha-linolenic acid (0.55 gr) was used as the fatty acid.

TABLE 10

The acidolysis activity of different enzymes using MCT and Arachidonic acid.

| Lipase origin | Conversion % (24 h) |
| --- | --- |
| *Aspergillus niger* | 3 |
| *Candida Antarctica* | 10 |
| *Candida cylindracea* | 3 |
| *Mucor miehei* | 3 |
| *Pseudomonas fluorescens* | 6 |
| *Pseudomonas cepacia* | 19 |
| *Rhizopus arrhizus* | 2 |
| *Rhizopus niveus* | 5 |
| Porcine pancreas lipase | 2 |
| *Aspergillus oryzae* | 6 |
| *Candida lipolytica* | 2 |
| *Mucor javanicus* | 6 |
| *Penicillium roqueforti* | 4 |
| *Rhizomucor miehei* | 15 |
| Wheat germ | 2 |
| *Chromobacterium viscosum* | 12 |
| Lipoprotein lipase *Pseudomonas* A | 7 |
| Lipoprotein lipase *Pseudomonas* B | 8 |

Reaction conditions as described in Table 1, with one modification, namely arachidonic acid (0.6 gr) was used as the fatty acid.

The results presented in Table 10 show that most lipases from the various sources did not catalyze the acidolysis of arachidonic acid and MCT as efficiently as in the other experiments disclosed hereinabove. This low acidolysis activity for the different lipases is common in circumstances where the fatty acid substrate contains high degree of unsaturation such that present in ARA, EPA and DHA. The results in Table 10 show that lipases extracted from *Pseudomonas cepacia, Rhizomucor miehei, Candida antarctica* and *Chromobacterium viscosum* are among the most efficient enzymes for the incorporation of ARA into MCT substrates. Lipases extracted from *Pseudomonas cepacia* and *Chromobacterium viscosum* are not certified for food applications, and therefore, the other two lipases are being used for acidolysis of ARA and MCT.

TABLE 11

The acidolysis activity of different enzymes using MCT and EPA.

| Lipase origin | Conversion % (24 h) |
| --- | --- |
| *Aspergillus niger* | 2 |
| *Candida Antarctica* | 22 |
| *Candida cylindracea* | 3 |
| *Mucor miehei* | 25 |
| *Pseudomonas fluorescens* | 3 |
| *Pseudomonas cepacia* | 25 |
| *Rhizopus arrhizus* | 22 |
| *Rhizopus niveus* | 2 |
| Porcine pancreas lipase | 3 |
| *Aspergillus oryzae* | 14 |
| *Candida lipolytica* | 3 |
| *Mucor javanicus* | 29 |
| *Penicillium roqueforti* | 7 |
| *Rhizomucor miehei* | 30 |
| Wheat germ | 3 |
| *Chromobacterium viscosum* | 25 |
| Lipoprotein lipase *Pseudomonas* A | 6 |
| Lipoprotein lipase *Pseudomonas* B | 14 |

Reaction conditions as described in Table 1, with one modification, namely EPA (0.6 gr) was used as the fatty acid.

TABLE 12

The acidolysis activity of different enzymes using MCT and DHA.

| Lipase origin | Conversion % (24 h) |
|---|---|
| *Aspergillus niger* | 2 |
| *Candida Antarctica* | 24 |
| *Candida cylindracea* | 2 |
| *Mucor miehei* | 27 |
| *Pseudomonas fluorescens* | 3 |
| *Pseudomonas cepacia* | 19 |
| *Rhizopus arrhizus* | 21 |
| *Rhizopus niveus* | 3 |
| Porcine pancreas lipase | 5 |
| *Aspergillus oryzae* | 2 |
| *Candida lipolytica* | 3 |
| *Mucor javanicus* | 2 |
| *Penicillium roqueforti* | 5 |
| *Rhizomucor miehei* | 16 |
| Wheat germ | 6 |
| *Chromobacterium viscosum* | 12 |
| Lipoprotein lipase *Pseudomonas* A | 11 |
| Lipoprotein lipase *Pseudomonas* B | 10 |

Reaction conditions as described in Table 1, with one modification, namely DHA (0.65 gr) was used as the fatty acid.

Tables 11 and 12 show that some lipases exhibit reliable acidolysis activity for EPA and DHA when both were separately interesterified with MCT. The results presented in Tables 11 and 12 show that lipases extracted from *Candida Antarctica, Mucor miehei, Pseudomonas Cepacia, Rhizopus arrhizus*, and *Rhizomucor miehei* are the most efficient enzymes for incorporation of DHA and EPA into MCT.

These results demonstrate that long-chain fatty acyl groups of different types can be efficiently incorporated in the sn-1 position of MCT molecules by using different lipases adapted to applications in organic media. The most active lipases that are certified for food applications and exchange medium-chain fatty acyl groups bound on the sn-1 position of MCT molecules with long-chain fatty acyl groups were identified and include those extracted from *Candida antarctica, Mucor miehei, Rhizopus arrhizus, Mucor javanicus, Rhizomucor miehei, Thermomyces lanuginose* and Lipoprotein lipase *Pseudomonas A*. The present results also demonstrate that the incorporation of polyunsaturated FAs (PUFAs) in MCT molecules is also possible using the adapted reaction system with adapted enzymes for organic synthesis.

Example 2

Synthesis of Structured Triglycerides

The acidolysis or inter-esterification reaction is initiated by adding 1 g immobilized lipase preparation to 10 g MCT and an equimolar amount of a free fatty acid or fatty acid ethyl ester. The reaction mixture is shaken at 50° C. for 2 to 8 hours. The immobilized enzyme is used repeatedly, i.e., the reaction is continued by leaving the immobilized enzyme in the reaction vessel after completion of the reaction, and replacing the reaction mixture with a freshly prepared reaction mixture comprising an MCT and a fatty acid or fatty acid ethyl ester. Thereafter, the triglyceride mixture is isolated using a molecular distillation system where the first distilled fraction at a temperature of 120° C. and a vacuum of 0.005 mmHg contains mainly the medium- and long-chain free fatty acids or their ethyl esters and partly the non-reacted MCT. The excess MCT in the medium is distilled at 200° C. and a pressure of 0.005 mmHg. The resulting oil contains mainly reacted MCT with one long-chain fatty acid at the sn-1 position (up to 80%) and also contains reacted MCT with two long-chain fatty acyl groups at the sn-1 and sn-3 positions. To protect the oil from oxidation, alpha tocopherol is added (2 mg per 1 g of structured oil) into the structured oil. This oil is sterilized prior to emulsification by filtration through a sterilizing filter (pore size 0.2 μm).

Example 3

Preparation of Structure Triglycerides of Predetermined Content of Fatty Acids The starting material MCTs composed of 58.3% C8 and 41.7% C10 (100 g, 0.2 mol) was mixed with a donor of a specific long-chain fatty acid, preferably a free fatty acid or ethyl fatty acid ester (0.24 mol). The solution was heated to 55° C. to obtain a homogenous mixture. A lipase (10 g) of 1,3-positional specificity, such as Lipozyme RM IM or any other lipase preparation was added to the reaction mixture. The reaction mixture was shaken at 55° C. for 8 hours. The enzyme was filtered off from the reaction medium for repeated use. The filtrate was subjected to molecular distillation where the first fraction was collected at a temperature of 120° C. and a pressure of 0.005 mmHg, which contained mainly the non-reacted fatty acids and the medium-chain fatty acids produced in the reaction. The second fraction was collected at a temperature of 200° C. and a pressure of 0.005 mmHg, which contained mainly the non-reacted MCTs. The residue of the distilled reaction mixture (approximately 90 g) mainly contained the MCTs predominantly monoacylated at the sn-1 position with the specific long-chain fatty acid (80-90%) and the MCTs predominantly diacylated at the sn-1 and sn-3 position (10-20%) with the specific long-chain fatty acid present in the starting material. Different proportions of reaction residues were mixed together to obtain the desired structured triglycerides composition with regard to the type, concentration and position on the glycerol backbone for the attached fatty acid. Alpha-tocopherol (2 mg/1 g of oil) was added to the structured triglycerides mixture prior to emulsification.

Example 4

Preparation of Structured Triglyceride Mixture Containing Arachidonic Acid

MCTs (100 g, 0.2 mol) and either Arachidonic acid (0.24 mol, free acid or its ethyl ester) or Martek's oil containing ARA and DHA each approximately 20% (50 g) were mixed together to obtain a homogenous solution. A lipase (10 g) of 1,3-positional specificity, such as Lipozyme RM IM or any other lipase preparation was added to the reaction mixture. The reaction mixture was shaken at 50° C. for 8 hours. The enzyme was filtered off from the reaction medium for repeated use. The filtrate was subjected to molecular distillation where the first fraction was collected at a temperature of 120° C. and a pressure of 0.005 mmHg, which contained mainly the unreacted fatty acids or their ethyl esters and the medium-chain fatty acids produced in the reaction. The second fraction was collected at a temperature of 200° C. and a pressure of 0.005 mm Hg, which contained mainly the non-reacted MCTs. The residue (approximately 90 g) mainly contained the MCTs predominantly monoacylated at the sn-1 position with the specific long-chain fatty acid (80-90%) and the MCTs predominantly diacylated at the sn-1 and sn-3 position (10-20%) with the specific long-chain fatty acid present in the starting material.

Example 5

Preparation of an Emulsion Comprising the Structured Triglycerides 200 g of the structured triglyceride preparation were prepared in a large volume according to the procedure disclosed hereinabove (Example 2). The structured triglycerides preparation was added to a homogenized mixture comprised of 22.5 g glycerol, 12 g phospholipid (Lipoid E 80) and 765.5 g distilled water adjusted to a desired pH value. The addition of sodium oleate (0.3 g) as an emulsion stabilizer into the mixture was optional. The mixture was homogenized several times with a homogenizer (Ultraturrax) at a rate of 10,000 rpm. In all steps adopted for preparation of the emulsion the temperature did not exceed 70° C. The obtained macro-emulsion was treated further in a high-pressure homogenizer (Microfluidizer) at 2600 psi for 5 minutes at temperature below 40° C. After this treatment the emulsion was passed through a membrane filter of pore size of 0.2 μm.

The composition of the parenteral nutrition is thus as follows:

Structured triglycerides—20% (w/v)
Alpha tocopherol—1.8 mg/1 g fatty acids
Phospholipids—12 g/liter
Glycerin—25 g/L
Water to complete to 1 liter.

After filling 200 ml aliquots of said lipid emulsion into plastic bags, the plastic bags are sterilized using high-pressure steam for 20 minutes at 121° C. to obtain a nutrition emulsion composition.

Example 6

Preparation of a Structured Triglyceride Composition

This example illustrates the fatty acid composition of structured triglycerides. As shown in Table 13, MCFA, LCFA, and VLCFA constitute 40-50%, 35-55%, and 4.5-5.5% by weight, respectively, of total FA in the structured triglycerides. The ratio of ω-6 to ω-3 fatty acids in the structured triglycerides is 1.75.

TABLE 13

| Fatty acid composition of structured triglycerides (% by weight). | | |
|---|---|---|
| Caproic acid | 6:0 | 0-5 |
| Caprylic acid | 8:0 | 20-30 |
| Capric acid | 10:0 | 10-30 |
| Lauric acid | 12:0 | 0-5 |
| Myristic acid | 14:0 | 0-5 |
| Palmitic acid | 16:0 | 5-30 |
| Palmitoleic acid | 16:1 | 0-5 |
| Stearic acid | 18:0 | 0-5 |
| Oleic acid | 18:1 | 10-30 |
| Linoleic acid | 18:2 ω-6 | 10-30 |
| Alpha linolenic acid | 18:3 ω-3 | 5-15 |
| Arachidonic acid (AA) | 20:4 ω-6 | 1-5 |
| Ecosapentaenoic acid (EPA) | 20:5 ω-3 | 0-5 |
| Docosahexaenoic acid (DHA) | 22:6 ω-3 | 1-5 |

Example 7

Preparation of a Structured Triglyceride Composition

This example illustrates the fatty acid composition of structured triglycerides. As shown in Table 14, MCFA, LCFA, and VLCFA constitute 45, 50.5, and 4.5% by weight, respectively, of total FA in the structured triglycerides. The ratio of ω-6 to ω-3 fatty acids in the structured triglycerides is 1.75.

TABLE 14

| Fatty acid composition of structured triglycerides (%). | | |
|---|---|---|
| Caproic acid | 6:0 | 2.5 |
| Caprylic acid | 8:0 | 30 |
| Capric acid | 10:0 | 10 |
| Lauric acid | 12:0 | 2.5 |
| Palmitic acid | 16:0 | 10 |
| Stearic acid | 18:0 | 2.5 |
| Oleic acid | 18:1 | 15 |
| Linoleic acid | 18:2 ω-6 | 16 |
| Alpha linolenic acid | 18:3 ω-3 | 7 |
| Arachidonic acid (AA) | 20:4 ω-6 | 1.5 |
| Ecosapentaenoic acid (EPA) | 20:5 ω-3 | 1.5 |
| Docosahexaenoic acid (DHA) | 22:6 ω-3 | 1.5 |

It will be appreciated by persons skilled in the art that the present invention is not limited by what has been particularly shown and described herein above. Rather the scope of the invention is defined by the claims that follow.

The invention claimed is:

1. A parenteral nutrition emulsion composition comprising a structured triglyceride, the structured triglyceride comprising a glycerol backbone having three fatty acid residues esterified thereto, wherein at least one fatty acid residue is selected from the group consisting of $C_6$-$C_{12}$ fatty acids and active derivatives thereof, and at least one fatty acid residue is selected from the group consisting of $C_{14}$-$C_{18}$ fatty acids, $C_{20}$-$C_{22}$ fatty acids, and active derivatives thereof, wherein the $C_{14}$-$C_{18}$ fatty acids and the $C_{20}$-$C_{22}$ fatty acids include ω-3 and ω-6 fatty acids, optionally in combination with ω-9 fatty acids, wherein the ω-6 fatty acids and the ω-3 fatty acids are present in the emulsion composition in a ratio of about 7:1 to about 1:1, with the proviso that a $C_{18}$-$C_{22}$ ω-3 fatty acid residue is not present on the same glycerol backbone together with gamma linolenic acid or dihomogamma linolenic acid, and further wherein the emulsion composition has a droplet size of less than about 1 μm.

2. The parenteral nutrition emulsion composition according to claim 1, comprising from about 9 to about 90% by weight $C_6$-$C_{12}$ fatty acids based on the weight of total fatty acids.

3. The parenteral nutrition emulsion composition according to claim 1, comprising from about 40 to about 50% by weight $C_6$-$C_{12}$ fatty acids based on the weight of total fatty acids.

4. The parenteral nutrition emulsion composition according to claim 1, comprising from about 9 to about 90% by weight $C_{14}$-$C_{18}$ fatty acids based on the weight of total fatty acids.

5. The parenteral nutrition emulsion composition according to claim 1, comprising from about 35 to about 55% by weight $C_{14}$-$C_{18}$ fatty acids based on the weight of total fatty acids.

6. The parenteral nutrition emulsion composition according to claim 1, comprising from about 1 to about 10% by weight $C_{20}$-$C_{22}$ fatty acids based on the weight of total fatty acids.

7. The parenteral nutrition emulsion composition according to claim 1, comprising from about 4.5 to about 5.5% by weight $C_{20}$-$C_{22}$ fatty acids based on the weight of total fatty acids.

8. The parenteral nutrition emulsion composition according to claim 1, wherein the ω-6 fatty acids and the ω-3 fatty acids are present in a ratio of about 2:1 to about 1.5:1.

9. The parenteral nutrition emulsion composition according to claim 1, wherein the structured triglyceride constitutes from about 10 to about 40% (w/v) of the composition.

10. The parenteral nutrition emulsion composition according to claim 1, wherein the structured triglyceride constitutes from about 20 to about 25% (w/v) of the composition.

11. The parenteral nutrition emulsion composition according to claim 1, wherein a droplet size of said emulsion is lower than about 0.22 μm.

12. The parenteral nutrition emulsion composition according to claim 1, further comprising tocopherol.

13. The parenteral nutrition emulsion according to claim 12, wherein the tocopherol is alpha tocopherol.

14. The parenteral nutrition emulsion according to claim 1, further comprising an emulsifier.

15. The parenteral nutrition emulsion according to claim 1, further comprising at least one component selected from the group consisting of surfactants, carbohydrates, vitamins, amino acids, trace minerals, osmolality modifiers and water.

16. The parenteral nutrition composition according to claim 1 comprising:
    (a) about 20% (w/v) structured triglycerides comprising:
        about 40-50% by weight $C_6$-$C_{12}$ fatty acids based on the weight of total fatty acids, wherein the $C_6$-$C_{12}$ fatty acids comprise 0-5% caproic acid, 20-30% caprylic acid, 10-30% capric acid, and 0-5% lauric acid by weight based on the weight of total fatty acids;
        about 35-55% by weight $C_{14}$-$C_{18}$ fatty acids based on the weight of total fatty acids, wherein the $C_{14}$-$C_{18}$ fatty acids comprise 0-5% mystiric acid, 5-30% palmitic acid, 0-5% palmitoleic acid, 0-5% stearic acid, 10-30% oleic acid, 10-30% linoleic acid, and 5-15% alpha linolenic acid by weight based on the weight of total fatty acids; and
        about 1-10% $C_{20}$-$C_{22}$ by weight fatty acids based on the weight of total fatty acids, wherein the $C_{20}$-$C_{22}$ fatty acids comprise 1-5% AA, 0-5% EPA, and 1-5% DHA by weight based on the weight of total fatty acids, wherein the ratio of ω-6 to ω-3 fatty acids is about 1:1 to about 2:1;
    (b) 1.2% (w/v) phospholipids;
    (c) 1.8-2.0 mg/1 g of fatty acids alpha tocopherol;
    (d) 0-25 g/L glycerin; and
    (e) water.

17. The parenteral nutrition emulsion composition according to claim 16 comprising:
    (a) about 20% (w/v) structured triglycerides comprising:
        about 45% by weight $C_6$-$C_{12}$ fatty acids based on the weight of total fatty acids, wherein the $C_6$-$C_{12}$ fatty acids comprise 2.5% caproic acid, 30% caprylic acid, 10% capric acid, and 2.5% lauric acid by weight based on the weight of total fatty acids;
        about 50% by weight $C_{14}$-$C_{18}$ fatty acids based on the weight of total fatty acids, wherein the $C_{14}$-$C_{18}$ fatty acids comprise 10% palmitic acid, 2.5% stearic acid, 15% oleic acid, 16% linoleic acid, and 7% alpha linolenic acid by weight based on the weight of total fatty acids; and
        about 5% by weight $C_{20}$-$C_{22}$ fatty acids based on the weight of total fatty acids, wherein the $C_{20}$-$C_{22}$ fatty acids comprise 1.5% AA, 1.5% EPA, and 1.5% DHA by weight based on the weight of total fatty acids, wherein the ratio of ω-6 to ω-3 fatty acids is 1.75;
    (b) about 1.2% (w/v) phospholipids;
    (c) about 1.8 mg/1 g of fatty acids alpha tocopherol;
    (d) about 10-25 g/L glycerin; and
    (e) water.

18. A parenteral nutrition emulsion composition comprising a structured triglyceride, the structured triglyceride comprising a glycerol backbone having three fatty acid residues esterified thereto, wherein at least one fatty acid residue is selected from the group consisting of $C_6$-$C_{12}$ fatty acids and active derivatives thereof in the internal position of the triglyceride backbone, and at least one fatty acid residue is selected from the group consisting of $C_{14}$-$C_{18}$ fatty acids, $C_{20}$-$C_{22}$ fatty acids, and active derivatives thereof in an external position of the triglyceride backbone, wherein the $C_{14}$-$C_{18}$ fatty acids and the $C_{20}$-$C_{12}$ fatty acids include ω-3 and ω-6 fatty acids, optionally in combination with ω-9 fatty acids, wherein the ω-6 fatty acids and the ω-3 fatty acids are present in the emulsion composition in a ratio of about 7:1 to about 1:1, and wherein the emulsion composition has a droplet size of less than about 1 μm.

19. The parenteral nutrition emulsion composition according to claim 18, comprising from about 9 to about 90% by weight $C_6$-$C_{12}$ fatty acids based on the weight of total fatty acids.

20. The parenteral nutrition emulsion composition according to claim 18, comprising from about 40 to about 50% by weight $C_6$-$C_{12}$ fatty acids based on the weight of total fatty acids.

21. The parenteral nutrition emulsion composition according to claim 18, comprising from about 9% to about 90% by weight $C_{14}$-$C_{18}$ fatty acids based on the weight of total fatty acids.

22. The parenteral nutrition emulsion composition according to claim 18, comprising from about 35% to about 55% by weight $C_{14}$-$C_{18}$ fatty acids based on the weight total fatty acids.

23. The parenteral nutrition emulsion composition according to claim 18, comprising from about 1% to about 10% by weight $C_{20}$-$C_{22}$ fatty acids based on the weight of total fatty acids.

24. The parenteral nutrition emulsion composition according to claim 18, comprising from about 4.5% to about 5.5% by weight $C_{20}$-$C_{22}$ fatty acids based on the weight of total fatty acids.

25. The parenteral nutrition emulsion composition according to claim 18, wherein the ω-6 fatty acids and the ω-3 fatty acids are present in a ratio of about 2:1 to about 1.5:1.

26. The parenteral nutrition emulsion composition according to claim 18, wherein the structured triglyceride constitutes from about 10 to about 40% (w/v) of the composition.

27. The parenteral nutrition emulsion composition according to claim 18, wherein the structured triglyceride constitutes from about 20 to about 25% (w/v) of the composition.

28. The parenteral nutrition emulsion composition according to claim 18, wherein a droplet size of said emulsion is lower than about 0.22 μm.

29. The parenteral nutrition emulsion composition according to claim 18, further comprising tocopherol.

30. The parenteral nutrition emulsion composition according to claim 29, wherein the tocopherol is alpha tocopherol.

31. The parenteral nutrition emulsion composition according to claim 18, further comprising an emulsifier.

32. The parenteral nutrition emulsion composition according to claim 18, further comprising at least one component selected from the group consisting of surfactants, carbohydrates, vitamins, amino acids, trace minerals, osmolality modifiers and water.

33. The parenteral nutrition emulsion composition according to claim 18 comprising:
(a) about 20% (w/v) structured triglycerides comprising:
about 40-50% by weight $C_6$-$C_{12}$ fatty acids based on the weight of total fatty acids, wherein the $C_6$-$C_{12}$ fatty acids comprise 0-5% caproic acid, 20-30% caprylic acid, 10-30% capric acid, and 0-5% lauric acid by weight based on the weight of total fatty acids;
about 35-55% by weight $C_{14}$-$C_{18}$ fatty acids based on the weight of total fatty acids, wherein the $C_{14}$-$C_{18}$ fatty acids comprise 0-5% mystiric acid, 5-30% palmitic acid, 0-5% palmitoleic acid, 0-5% stearic acid, 10-30% oleic acid, 10-30% linoleic acid, and 5-15% alpha linolenic acid by weight based on the weight of total fatty acids; and
about 1-10% $C_{20}$-$C_{22}$ by weight fatty acids based on the weight of total fatty acids, wherein the $C_{20}$-$C_{22}$ fatty acids comprise 1-5% AA, 0-5% EPA, and 1-5% DHA by weight based on the weight of total fatty acids, wherein the ratio of ω-6 to ω-3 fatty acids is 1:1-2:1;
(b) 1.2% (w/v) phospholipids;
(c) 1.8-2.0 mg/1 g of fatty acids alpha tocopherol;
(d) 0-25 g/L glycerin; and
(e) water.

34. The parenteral nutrition emulsion composition according to claim 33 comprising:
(a) about 20% (w/v) structured triglycerides comprising:
about 45% by weight $C_6$-$C_{12}$ fatty acids based on the weight of total fatty acids, wherein the $C_6$-$C_{12}$ fatty acids comprise 2.5% caproic acid, 30% caprylic acid, 10% capric acid, and 2.5% lauric acid by weight based on the weight of total fatty acids;
about 50% by weight $C_{14}$-$C_{18}$ fatty acids based on the weight of total fatty acids, wherein the $C_{14}$-$C_{18}$ fatty acids comprise 10% palmitic acid, 2.5% stearic acid, 15% oleic acid, 16% linoleic acid, and 7% alpha linolenic acid by weight based on the weight of total fatty acids; and
about 5% by weight $C_{20}$-$C_{22}$ fatty acids based on the weight of total fatty acids, wherein the $C_{20}$-$C_{22}$ fatty acids comprise 1.5% AA, 1.5% EPA, and 1.5% DHA by weight based on the weight of total fatty acids, wherein the ratio of ω-6 to ω-3 fatty acids is 1.75;
(b) about 1.2% (w/v) phospholipids;
(c) about 1.8 mg/1 g of fatty acids alpha tocopherol;
(d) about 10-25 g/L glycerin; and
(e) water.

35. A method of providing nutrition to a subject in need thereof comprising parenterally administering to the subject a parenteral nutrition emulsion composition according to claim 18.

36. The method according to claim 35, wherein the subject is an AIDS patient.

37. The parenteral nutrition emulsion composition according to claim 33 comprising:
(a) about 20% (w/v) structured triglycerides comprising:
about 45% by weight $C_6$-$C_{12}$ fatty acids based on the weight of total fatty acids, wherein the $C_6$-$C_{12}$ fatty acids comprise about 25% caprylic acid and 20% capric acid by weight based on the weight of total fatty acids;
about 45% by weight $C_{14}$-$C_{18}$ fatty acids based on the weight of total fatty acids, wherein the $C_{14}$-$C_{18}$ fatty acids comprise about 10% palmitic acid, 15% oleic acid, 10% linoleic acid, and 10% alpha linolenic acid by weight based on the weight of total fatty acids; and
about 10% by weight $C_{20}$-$C_{22}$ fatty acids based on the weight of total fatty acids, wherein the $C_{20}$-$C_{22}$ fatty acids comprise 3% AA, 1.5% EPA, and 3% DHA by weight based on the weight of total fatty acids, wherein the ratio of ω-6 to ω-3 fatty acids is 1;
(b) about 1.2% (w/v) phospholipids;
(c) about 1.8 mg/1 g of fatty acids alpha tocopherol;
(d) about 10-25 g/L glycerin; and
(e) water.

38. The method according to claim 35, wherein the subject is a preterm or term infant.

39. A method of providing nutrition to a subject in need thereof comprising parenterally administering to the subject a parenteral nutrition emulsion composition according to claim 1.

40. The parenteral nutrition emulsion composition of claim 1, wherein the $C_{14}$-$C_{18}$ fatty acids and the $C_{20}$-$C_{22}$ fatty acids include ω-9 fatty acids in combination with the ω-3 and ω-6 fatty acids.

41. The parenteral nutrition emulsion composition of claim 18, wherein the $C_{14}$-$C_{18}$ fatty acids and the $C_{20}$-$C_{22}$ fatty acids include ω-9 fatty acids in combination with the ω-3 and ω-6 fatty acids.

* * * * *

UNITED STATES PATENT AND TRADEMARK OFFICE
CERTIFICATE OF CORRECTION

PATENT NO. : 7,919,526 B2
APPLICATION NO. : 10/591734
DATED : April 5, 2011
INVENTOR(S) : Rozen et al.

It is certified that error appears in the above-identified patent and that said Letters Patent is hereby corrected as shown below:

On the Title Page:
Before Item (51), insert the following:
    Item -- (60)     Related U.S. Application Data
        Provisional application no. 60/549,550, filed Mar. 4, 2004 --.

Column 28:
Line 18 (claim 18, line 11), change "$C_{20}$-$C_{12}$" to -- $C_{20}$-$C_{22}$ --.

Signed and Sealed this
Seventeenth Day of May, 2011

David J. Kappos
*Director of the United States Patent and Trademark Office*